(12) United States Patent
Sakai et al.

(10) Patent No.: US 8,612,030 B2
(45) Date of Patent: Dec. 17, 2013

(54) HEALTH EXERCISE ASSIST SYSTEM, PORTABLE MUSIC PLAYBACK APPARATUS, SERVICE INFORMATION PROVIDING APPARATUS, INFORMATION PROCESSING APPARATUS, AND HEALTH EXERCISE ASSIST METHOD

(75) Inventors: Yuichi Sakai, Kanagawa (JP); Katsuya Shirai, Kanagawa (JP); Yoichiro Sako, Tokyo (JP); Masamichi Asukai, Kanagawa (JP); Akane Sano, Tokyo (JP); Motoyuki Takai, Tokyo (JP); Makoto Inoue, Tokyo (JP)

(73) Assignee: Sony Corporation, Tokyo (JP)

( * ) Notice: Subject to any disclaimer, the term of this patent is extended or adjusted under 35 U.S.C. 154(b) by 1139 days.

(21) Appl. No.: 11/836,384

(22) Filed: Aug. 9, 2007

(65) Prior Publication Data

US 2008/0051919 A1  Feb. 28, 2008

(30) Foreign Application Priority Data

Aug. 22, 2006 (JP) ................................ 2006-224891

(51) Int. Cl.
*G06F 17/00* (2006.01)
(52) U.S. Cl.
USPC .......................................................... 700/94
(58) Field of Classification Search
USPC ..................... 700/94; 715/760; 705/2, 27
See application file for complete search history.

(56) References Cited

U.S. PATENT DOCUMENTS

| | | | | |
|---|---|---|---|---|
| 6,585,622 | B1 * | 7/2003 | Shum et al. | 482/8 |
| 2006/0253210 | A1 * | 11/2006 | Rosenberg | 700/94 |
| 2007/0118043 | A1 * | 5/2007 | Oliver et al. | 600/519 |
| 2007/0271065 | A1 * | 11/2007 | Gupta et al. | 702/160 |
| 2007/0271116 | A1 * | 11/2007 | Wysocki et al. | 705/2 |
| 2009/0024233 | A1 * | 1/2009 | Shirai et al. | 700/94 |
| 2009/0144080 | A1 * | 6/2009 | Gray et al. | 705/2 |

FOREIGN PATENT DOCUMENTS

| | | |
|---|---|---|
| JP | 2002-34934 | 2/2002 |
| JP | 2003-24467 | 1/2003 |
| JP | 2003-305146 | 10/2003 |
| JP | 2004-318534 | 11/2004 |
| JP | 2005-156641 | 6/2005 |

* cited by examiner

*Primary Examiner* — Andrew C Flanders
(74) *Attorney, Agent, or Firm* — Oblon, Spivak, McClelland, Maier & Neustadt, L.L.P.

(57) ABSTRACT

In a health exercise assist system, a portable music playback apparatus acquires a preset exercise plan, a history of exercise information, and a music playback history and stores them. An information processing apparatus produces a service request including at least one of the preset exercise plan, the history of exercise information, and the music playback history acquired from the portable music playback apparatus, and transmits it to a service information providing apparatus. In accordance with the service request received from the information processing apparatus, the service information providing apparatus produces service information and returns the produced service information to the information processing apparatus. The information processing apparatus provides the received service information to a user of the audio playback apparatus.

19 Claims, 29 Drawing Sheets

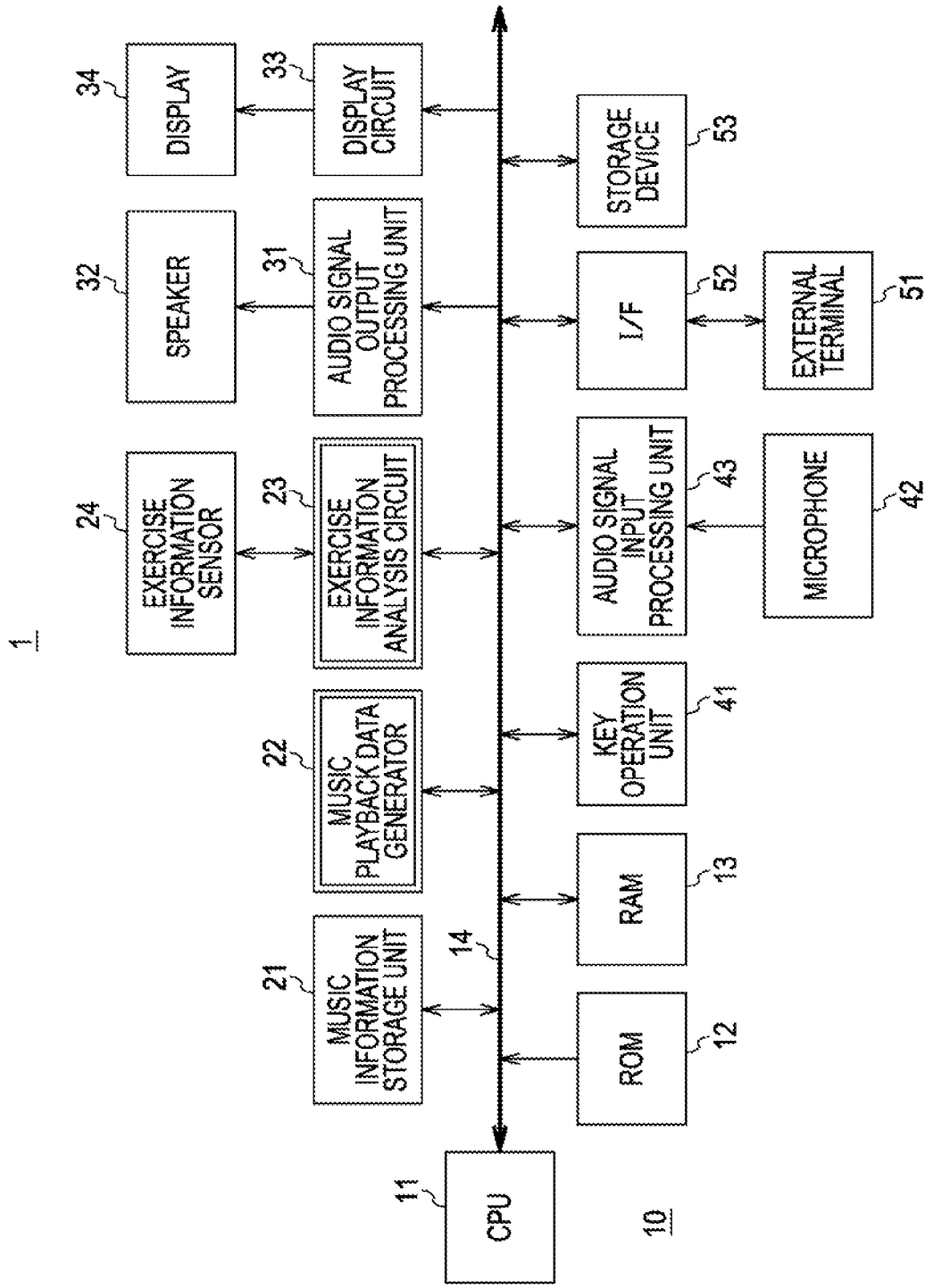

FIG. 6A

INPUT YOUR PROFILE

NAME  
SEX  
AGE  
HEIGHT         cm  
WEIGHT         kg

| NAME | ○○○ |
|---|---|
| SEX | Man |
| AGE | 30 |
| HEIGHT | 170 cm |
| WEIGHT | 60 kg |
| BMI | 20.8 |
| DEGREE OF OBESITY | 1 |

OK?  YES  NO

INPUT TARGET AMOUNT OF EXERCISE

[　　] HOURS   [　　] MINUTES

INPUT TARGET CALORIES TO BE CONSUMED

[　　] cal

TARGET AMOUNT OF EXERCISE

[ 00 ] HOURS   [ 25 ] MINUTES

TARGET CALORIES TO BE CONSUMED

[ 770 ] cal

OK?  [ YES ]  [ NO ]

INPUT TYPE OF EXERCISE AND TIME
DURING WHICH TO PERFORM EXERCISE

TYPE OF EXERCISE        EXERCISE TIME

[         ]             [      ] MINUTES

[ADD]   [END]

1. JOGGING        5 MINUTES
2. RUNNING       20 MINUTES
3. JOGGING        5 MINUTES
-------------------- END --------------------

OK?  [YES]  [NO]

| MUSIC NAME | MUSIC TEMPO | LENGTH (PLAY TIME) | GENRE | PERFORMER |
|---|---|---|---|---|
| MUSIC A | 82 | 3 min 00 sec | POP | a |
| MUSIC B | 120 | 4 min 00 sec | POP | a |
| MUSIC C | 81 | 2 min 56 sec | J-POP | b |
| MUSIC D | 79 | 4 min 32 sec | BALLAD | k |
| MUSIC E | 100 | 1 min 53 sec | JAZZ | g |
| MUSIC F | 81 | 5 min 47 sec | HIP-HOP | m |
| ⋮ | ⋮ | ⋮ | ⋮ | ⋮ |

FIG. 10A

| MUSIC NAME | PLAY TIME | TEMPO |
|---|---|---|
| MUSIC A | 3 min 00 sec | 82 |
| MUSIC C | 2 min 56 sec | 81 |
| MUSIC F | 5 min 47 sec | 81 |

FIG. 10B

| MUSIC NAME | PLAY TIME | TEMPO | GENRE | PERFORMER |
|---|---|---|---|---|
| MUSIC A | 3 min 00 sec | 82 | POP | a |
| MUSIC B | 4 min 00 sec | 120 | POP | a |

FIG. 11

| MUSIC NAME | ○○○ |
| --- | --- |
| ARTIST NAME | △△△ |
| GENRE | ×× × |
| TEMPO | 120 BPM |
| TYPE OF EXERCISE | JOGGING |
| STRENGTH OF EXERCISE | 5.0 METS |

EXERCISE INFORMATION IS DISPLAYED BELOW

| EXERCISE TIME | 30:00 min |
| --- | --- |
| WAKING DISTANCE | 3.00 km |
| AVERAGE SPEED | 6.00 km/h |
| CONSUMED CALORIES | 150 kcal |
| REMOVED FAT | 19.5 g |

GOOD EXERCISE TODAY!

PLAN FOR SECOND-TIME EXERCISE (YYMMDDHHMM)
JOGGING 5 min + RUNNING 20 min + JOGGING 5 min PLAN FOR FIRST-TIME EXERCISE (YYMMDDHHMM)
TIME: 25 min, CALORIES TO BE CONSUMED: 770 cal

...

HISTORY OF SECOND-TIME EXERCISE

HISTORY OF FIRST-TIME EXERCISE

| MUSIC NAME | TEMPO | PLAY TIME | RUNNING TYPE | EXERCISE TEMPO (PLANNED) | RUNNING TYPE (ACTUALLY DETECTED) | NUMBER OF STEPS (CALCULATED VALUE) |
|---|---|---|---|---|---|---|
| MUSIC A | 82 | 3 min 00 sec | WALKING | 82 | WALKING | 246 |
| MUSIC C | 81 | 5 min 52 sec | JOGGING | 82 | JOGGING | 481 |
| MUSIC B | 120 | 8 min 00 sec | RUNNING | 117 | JOGGING | 936 |
| MUSIC H | 100 | 1 min 53 sec | JOGGING | 100 | JOGGING | 188 |
| MUSIC L | 81 | 5 min 47 sec | JOGGING | 85 | JOGGING | 492 |
| ... | ... | ... | ... | ... | ... | ... |

FIG. 14

WALKING DISTANCE

STEP SIZE = HEIGHT × 0.45 (WHEN WALKING)     ... (1)
    STEP SIZE = HEIGHT × 0.50 (WHEN JOGGING)     ... (2)

WALKING DISTANCE = STEP SIZE × NUMBER OF STEPS   ... (3)

(EXAMPLE) WHEN PERSON WITH HEIGHT OF 170 cm WALKS FOR 2 min 30 sec IN SYNCHRONIZATION WITH MUSIC WITH TEMPO OF 120, WALKING DISTANCE IS CALCULATED AS 170 cm × 0.45 × 120 × (2 × 60 + 30 (sec))
    ÷ 60 (sec) = 22950 cm = 229.5 m     ... (4)

(EXAMPLE) WHEN PERSON WITH A HEIGHT OF 170 cm RUNS FOR 2 min 30 sec IN SYNCHRONIZATION WITH MUSIC WITH TEMPO OF 170, WALKING DISTANCE IS CALCULATED AS 170 cm × 0.50 × 170 × (2 × 60 + 30 (sec))
    ÷ 60 (sec) = 36125 cm = 361.24 m     ... (5)

FIG. 15

AVERAGE SPEED

AVERAGE SPEED = WALKING DISTANCE / EXERCISE TIME (IN TOTAL)   ... (6)

(EXAMPLE) AVERAGE SPEED FOR 3-km WALK IN 30 min IS CALCULATED AS 3.00 km / 0.5 (hr) = 6.00 km/hr     ... (7)

FIG. 16

CONSUMED ENERGY PER MINUTE $\quad$ Wmin = (35 + SPEED (m/min)) ÷ 2000 × WEIGHT (kg) $\quad\quad$ ... (8)

$\quad$ (EXAMPLE) IF PERSON WITH WEIGHT OF 68 kg WALKS FOR 60 min AT SPEED OF 100 m/min, CONSUMED ENERGY IS CALCULATED AS $\quad$ Wmin = (35 + 100) ÷ 2000 × 68 = 4.59 kcal/min $\quad\quad$ ... (9)
$\quad$ Wtotal = 4.59 kcal/min × 60 min = 275.5 kcal $\quad\quad$ ... (10)

FIG. 17

CONSUMED ENERGY (CALCULATED USING MET VALUE)

$\quad$ CONSUMED ENERGY (kcal)
$\quad$ = WEIGHT (kg) × MET VALUE × EXERCISE TIME (hr) $\quad\quad$ ... (11)

$\quad$ (EXAMPLE) WHEN PERSON WITH WEIGHT OF 60 kg PERFORMS EXERCISE WITH MET VALUE OF 5 FOR 30 min, CONSUMED ENERGY IS CALCULATED AS $\quad\quad$ 60 × 5 × 0.5 = 150 kcal $\quad\quad$ ... (12)

$\quad\quad$ MET VALUE $\quad$ WALKING: 4 TO 7
$\quad\quad\quad\quad\quad\quad\quad\quad$ JOGGING: 7 TO 15

$\quad$ (EXAMPLE) IN EXAMPLE SHOWN IN FIG. 8, IF WEIGHT OF USER IS EQUAL TO 60 kg, THEN CONSUMED ENERGY IS CALCULATED AS $\quad\quad$ 60 × (3 × 3.5 + 4 × 5.0 + 2.93 × 3.5 + 4.53 × 3.0 + 1.88
$\quad\quad$ × 4.0 + 5.78 × 3.5) / 60 = 82.095 $\quad\quad$ ... (13)

FIG. 18

AMOUNT OF BURNT FAT

CALORIES NECESSARY TO BURN 1 kg OF FAT: 7700 kcal

AMOUNT OF BURNT FAT = CONSUMED ENERGY (kcal) ÷ 7700 kcal × 1000 g ... (14)

(EXAMPLE)　IN THE EXAMPLE SHOWN IN FIG. 8
(IN WHICH CONSUMED ENERGY = 155.5 kcal)

AMOUNT OF FAT BURNT BY EXERCISE = 82.095 kcal ÷ 7700 kcal × 1000 g
= 10.66 g　　... (15)

FIG. 19

STRENGTH OF EXERCISE MEASURED IN METS (METABOLIC EQUIVALENTS)

MET VALUE = AMOUNT OF OXYGEN CONSUMED DURING EXERCISE /
AMOUNT OF OXYGEN CONSUMED IN RESTING STATE = (R + H + V) / R　... (16)

ONE MET CORRESPONDS TO CONSUMPTION OF OXYGEN OF 3.5 ml/kg·min

AMOUNT OF OXYGEN CONSUMED DURING EXERCISE = R + H + V (ml/kg·min) ... (17)

R: AMOUNT OF OXYGEN CONSUMED IN RESTING STATE (3.5 ml/kg·min)
H: HORIZONTAL MOTION COMPONENT
　　0.1 × SPEED V (m/min) (WALKING)　　　　　　　... (18)
　　0.2 × SPEED V (m/min) (RUNNING)　　　　　　　... (19)
V: VERTICAL MOTION COMPONENT
　　0.9 × SPEED V (m/min) × TILT rad (%)　　　　　... (20)

FIG. 20

(EXAMPLE) MET VALUE WHEN WALKING IS PERFORMED AT A SPEED OF 6 km/h $\quad$ HORIZONTAL COMPONENT H = 0.1 × 100 = 10.0 ... (21)
$\quad$ VERTICAL ELEMENT V = 0.9 × 100 × 0 = 0.0 ... (22)
$\quad$ TOTAL = 3.5 + 10.0 + 0.0 = 13.5 ... (23)
$\quad$ MET VALUE = 13.5 / 3.5 = 3.9 ... (24)

(EXAMPLE) MET VALUE WHEN JOGGING IS PERFORMED AT A SPEED OF 10 km/h $\quad$ HORIZONTAL COMPONENT H = 0.2 × 166.7 = 33.34 ... (25)
$\quad$ VERTICAL ELEMENT V = 0.9 × 166.7 × 0 = 0.0 ... (26)
$\quad$ TOTAL = 3.5 + 33.34 = 36.84 ... (27)
$\quad$ MET VALUE = 36.84 / 3.5 = 10.5 ... (28)

FIG. 21

(EXAMPLE) WHEN A PERSON WITH A WEIGHT OF 60 kg RUNS ON A LEVEL PLACE AT A SPEED OF 10 km/h (166.7 m/min) FOR 30 min, $\quad$ (3.5 + 166.7 × 0.2) / 3.5 × 60 × 30 / 60 = 315.77 kcal ... (29)

FIG. 22

CALCULATION OF ENERGY CONSUMED DURING EXERCISE (USING MET VALUE)

$\quad$ SPEED OF EACH MOTION Vi = STEP SIZE Ww / TIME OF EACH MOTION Ti ... (30)

$\quad$ ENERGY CONSUMED = SUM OF (WEIGHT (kg) × MET VALUE DETERMINED
$\quad\quad\quad\quad\quad\quad\quad\quad\quad$ FROM SPEED OF EACH MOTION Vi
$\quad\quad\quad\quad\quad\quad\quad\quad\quad$ × TIME OF EACH MOTION Ti) ... (31)

$\quad\quad\quad\quad\quad\quad\quad$ = ΣWEIGHT × METS (Vi) × Ti ... (32)

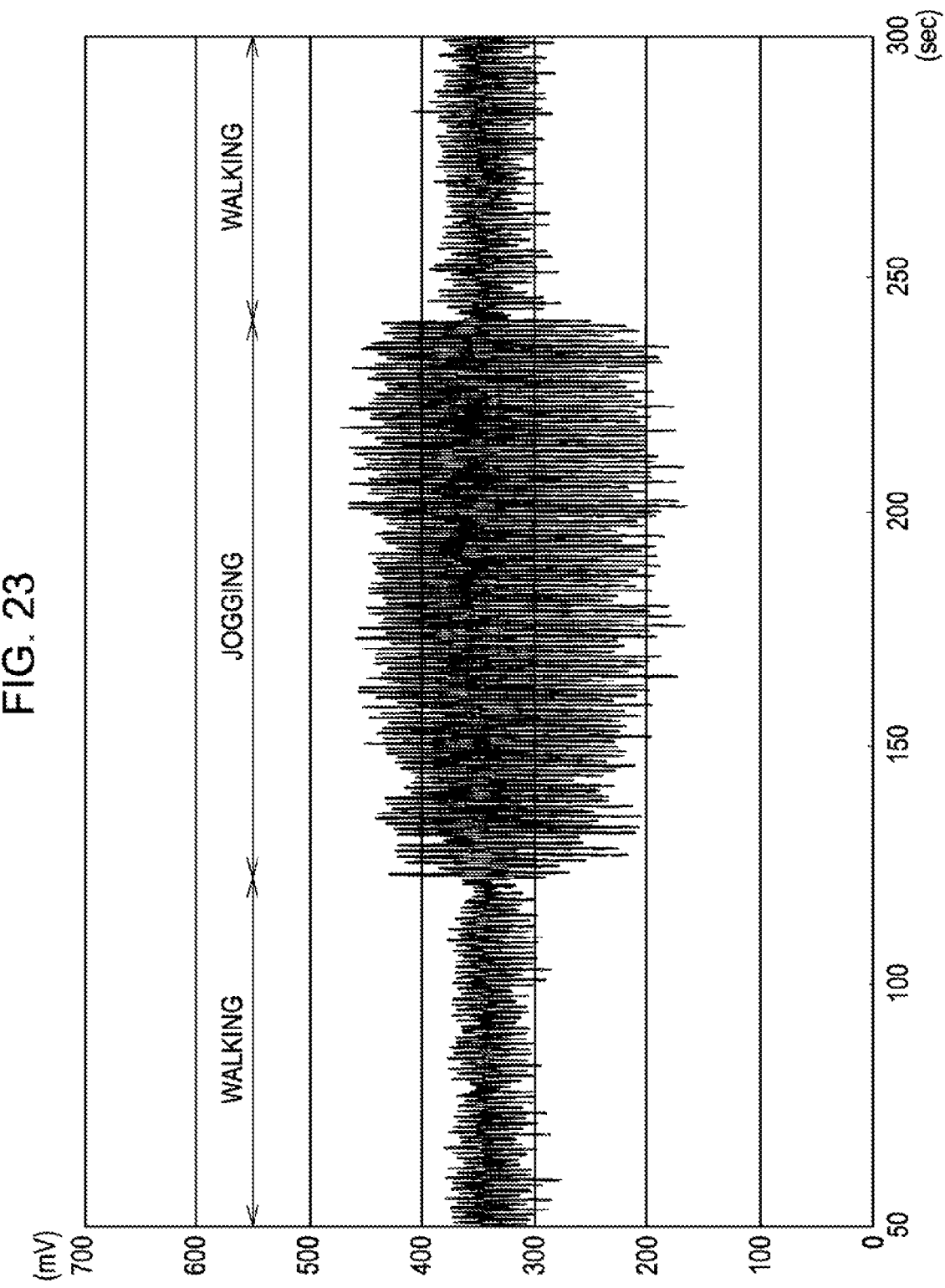

- GOAL ACHIEVEMENT MESSAGE
- REWARDING OF CONTENT AND POINT

- NUMBER OF ELAPSED DAYS
- NUMBER OF STEPS ACHIEVED TODAY
- NEXT PLACE TO VISIT
- DISPLAY ACHIEVED PART ALONG WHOLE COURSE ON MAP
- PROVIDE PICTURE OF PILGRIMAGE PLACE AND HISTORY THEREOF
- GIVE POINTS DEPENDING ON SITUATION

- NUMBER OF STEPS WALKED EACH DAY
- CALORIES CONSUMED EACH DAY
- BRIEF ADVICE
- ETC.

- NUMBER OF STEPS TODAY
- CUMULATIVE TOTAL NUMBER OF STEPS
- ADVERTISEMENT AREA
- OTHER ITEMS
  - REMAINING NUMBER OF STEPS
  - PREDICTED PROGRESS TOWARD GOAL

FIG. 31A

```
DATE (YEAR-MONTH-DAY): 2006-7-8
COMMENT: · · · · · · · · · · · · · · · · · · · · · · ·
· · · · · · · · · · · ·
MUSIC PLAYED TODAY: MUSIC A, MUSIC B, MUSIC C, · · · ·
NUMBER OF STEPS WALKED TODAY: 7089
CALORIES CONSUMED: 2000
    ·
    ·
    ·
```

FIG. 31B

```
EXERCISE DIARY          JULY 8, 2006
 · COMMENT: · · · · · · · · · · · · · · · · · · · · · ·
     · · · · · · · · · · ·
 · MUSIC PLAYED TODAY: MUSIC A, MUSIC B, MUSIC C, · · · ·
 · NUMBER OF STEPS WALKED TODAY: 7089
 · CALORIES CONSUMED: 2000

EXERCISE DIARY          JULY 8, 2006
 · COMMENT: · · · · · · · · · · · · · · · · · · · · · ·
     · · · · · · · · · · ·
 · MUSIC PLAYED TODAY: MUSIC A, MUSIC B, MUSIC E, MUSIC G, · · · ·
 · NUMBER OF STEPS WALKED TODAY: 9650
 · CALORIES CONSUMED: 2400
         ·
         ·
         ·
```

FIG. 35

```
SIMPLIFIED CALCULATION OF CONSUMED ENERGY

USING ASSUMED SPEED OR STEP SIZE

○ WALKING
    WHEN WALKING STEP SIZE IS ASSUMED TO BE 0.7 m
```

CALORIES CONSUMED = 0.5 × WEIGHT (kg) × DISTANCE (km)  ... (33)
= 0.00035 × WEIGHT (kg) × NUMBER OF STEPS ... (34)

WHEN WALKING SPEED IS ASSUMED TO BE 4 km/h

CALORIES CONSUMED = 0.5 × WEIGHT (kg) × DISTANCE (km)  ... (35)
= 0.033 × WEIGHT (kg) × TIME (min)  ... (36)

○ JOGGING
    WHEN JOGGING STEP SIZE IS ASSUMED TO BE 0.7 m

CALORIES CONSUMED = 1.05 × WEIGHT (kg) × DISTANCE (km)  ... (37)
= 0.0007 × WEIGHT (kg) × NUMBER OF STEPS  ... (38)

WHEN JOGGING SPEED IS ASSUMED TO BE 8 km/h

CALORIES CONSUMED = 1.0 × WEIGHT (kg) × DISTANCE (km)  ... (39)
= 0.013 × WEIGHT (kg) × TIME (min)  ... (40)

HEALTH EXERCISE ASSIST SYSTEM, PORTABLE MUSIC PLAYBACK APPARATUS, SERVICE INFORMATION PROVIDING APPARATUS, INFORMATION PROCESSING APPARATUS, AND HEALTH EXERCISE ASSIST METHOD

CROSS REFERENCES TO RELATED APPLICATIONS

The present invention contains subject matter related to Japanese Patent Application JP 2006-224891 filed in the Japanese Patent Office on Aug. 22, 2006, the entire contents of which are incorporated herein by reference.

BACKGROUND OF THE INVENTION

1. Field of the Invention

The present invention relates to a system, apparatus, and method for assisting a user to exercise while listening to music.

2. Description of the Related Art

It is known to perform exercise such as walking or jogging while listening to music with a tempo well matching a tempo of music thereby leveling the tempo of exercise in synchronization with music and thus reducing a load imposed on an exercising person. To make it possible to easily use this technique, Japanese Unexamined Patent Application Publication No. 2005-156641 discloses a technique to control the tempo of music being played in accordance with a walking pace.

To make it possible for a user to perform a particular amount of exercise at a moderate pace, Japanese Unexamined Patent Application Publication No. 2003-024467 discloses a technique to advance a virtual reality game with advance in an exercise menu so that the user can continue exercise while enjoying the virtual reality game.

The techniques disclosed in Japanese Unexamined Patent Application Publication No. 2005-156641 and Japanese Unexamined Patent Application Publication No. 2003-024467 are advantageous in that instead of patiently performing monotonous exercise according to an exercise plan in terms of an exercise time, a moving distance, the number of times, etc., a user can enjoy performing exercise until a goal is achieved.

SUMMARY OF THE INVENTION

In order to maintain or further enhance health, it is important to continuously perform everyday exercise for a rather long period such as several weeks or several months. If exercise is performed not constantly but occasionally, the exercise is not very useful in maintaining or enhancing health.

Thus, it is desirable to give an effective incentive to an exerciser so that the exerciser is motivated to continue everyday exercise for a long period.

In view of the above, it is desirable to provide a technique to provide information or service to a user depending on exercise performed by the user to assist the user to continue everyday exercise for a long period.

According to an embodiment of the present invention, there is provided a health exercise assist system including a portable music playback apparatus, a service information providing apparatus, and an information processing apparatus, wherein the portable music playback apparatus includes a detection unit adapted to detect exercise information associated with a physical exercise performed by a user, a music playback unit adapted to select music to be played and play the selected music, and a storage unit adapted to store a preset exercise plan, a history of exercise information detected by the detection unit, and a music playback history of music played by the music playback unit, and an information output unit adapted to output information stored in the storage unit, the service information providing apparatus includes an information input unit adapted to receive information from the portable music playback apparatus via the information processing apparatus, the information including at least one of the following pieces of information, the exercise plan, the history of exercise information, and the music playback history, a service information producing unit adapted to produce service information to be provided to a user of the portable music playback apparatus, in accordance with the information accepted via the information input unit, and, a service information output unit adapted to output the service information, and the information processing apparatus includes an information input unit adapted to receive information from the portable music playback apparatus, the information including at least one of the following pieces of information, the exercise plan, the history of exercise information, and the music playback history, a transmitting unit adapted to transmit the information input via the information input unit to the service information providing apparatus, a receiving unit adapted to receive the service information output from the service information providing apparatus, and providing means for providing the service information to the user.

In this health exercise assist system, the portable music playback apparatus plays music via the music playback unit so that the user of the portable music playback apparatus can perform exercise while listening to music played by the portable music playback apparatus. When the user is performing exercise, exercise information associated with the exercise performed by the user is detected by the detection unit. The preset exercise plan, the history of the detected exercise information, and the history of playback of music are stored in the storage unit and output to the information processing apparatus via the information output means.

The service information providing apparatus is, for example, a server located on a wide-area network such as the Internet. As described in further detail later, if the service information providing apparatus receives information including at least one of the exercise plan, the history of the detected exercise information, and the history of playback of music from the portable music playback apparatus via the information processing apparatus, the service information producing unit of the service information providing apparatus produces service information on the basis of the received information. The resultant produced service information is returned to the information processing apparatus via the service information output unit.

The information processing apparatus is, for example, a personal computer installed at the home or the like of the user of the portable music playback apparatus. If the information processing apparatus receives, via the information input unit, information which was output from the portable music playback apparatus and which includes at least one of the exercise plan, the history of the detected exercise information, and the history of playback of music, the information processing apparatus transfers the received information to the service information providing apparatus via the network. If the information processing apparatus receives service information returned from the service information providing apparatus, the information processing apparatus provides the received service information to the user via the providing means.

As described above, the portable music playback apparatus provides at least one of the exercise plan, the history of the exercise information detected by the detection unit, and the history of music played by the music playback unit to the service information providing apparatus via the information processing apparatus. In response, the service information providing apparatus provides service information to the information processing apparatus. The service information is provided to the user of the portable music playback apparatus via the information processing apparatus.

The service information produced by the service information providing apparatus varies depending on the information including at least one of the exercise plan, the history of the exercise information, and the music playback history provided from the portable music playback apparatus such that a privilege, a goal, or useful information is given to the user of the portable music playback apparatus to motivate the user to continue the everyday exercise for a long term without causing overload to be imposed on the user.

BRIEF DESCRIPTION OF THE DRAWINGS

FIG. 2 is a block diagram illustrating an audio playback apparatus;

FIGS. 6A and 6B are diagrams illustrating an example of a manner in which an audio playback apparatus acquires a personal profile;

FIGS. 7A and 7B are diagrams illustrating an example of a manner in which an audio playback apparatus acquires a target amount of exercise;

FIGS. 8A and 8B are diagrams illustrating an example of a manner in which an audio playback apparatus acquires a target amount of exercise;

FIG. 9 is a diagram illustrating an example of a music information list which is a list of music playable by an audio playback apparatus;

FIGS. 10A and 10B illustrate examples of playlists produced in an audio playback apparatus;

FIG. 11 is a diagram illustrating an example of information associated with music being played, which is displayed on an audio playback apparatus;

FIG. 12 is diagram illustrating an example of information associated with an amount of exercise, displayed on an audio playback apparatus;

FIGS. 13A and 13B illustrate examples of history information stored in an audio playback apparatus;

FIG. 14 illustrates examples of calculation of a walking distance;

FIG. 15 illustrates an example of a calculation of the average moving speed during exercise;

FIG. 16 illustrates an example of calculation of consumption energy using energy consumed every minute;

FIG. 17 illustrates examples of calculation of consumption energy using a MET value indicating exercise strength determined for each exercise type;

FIG. 18 illustrates an example of calculation of amount of fat burnt;

FIG. 19 is a diagram provided for an explanation of the MET value;

FIG. 20 illustrates examples of calculation of a MET value;

FIG. 21 illustrates an example of calculation of consumption energy in calories;

FIG. 22 illustrates an example of calculation of consumption energy in calories;

FIG. 23 is a graph illustrating a vertical component of acceleration detected by a three-axis acceleration sensor disposed as an exercise information sensor;

FIGS. 31A and 31B illustrate specific examples of services provided by service information providing apparatus;

FIG. 35 illustrates examples of simplified calculations of consumption energy of a user;

DESCRIPTION OF THE PREFERRED EMBODIMENTS

A system, an apparatus, and a method according to embodiments of the present invention are described below with reference to the accompanying drawings.

Overview of Health Exercise Assist System

Figure 1:
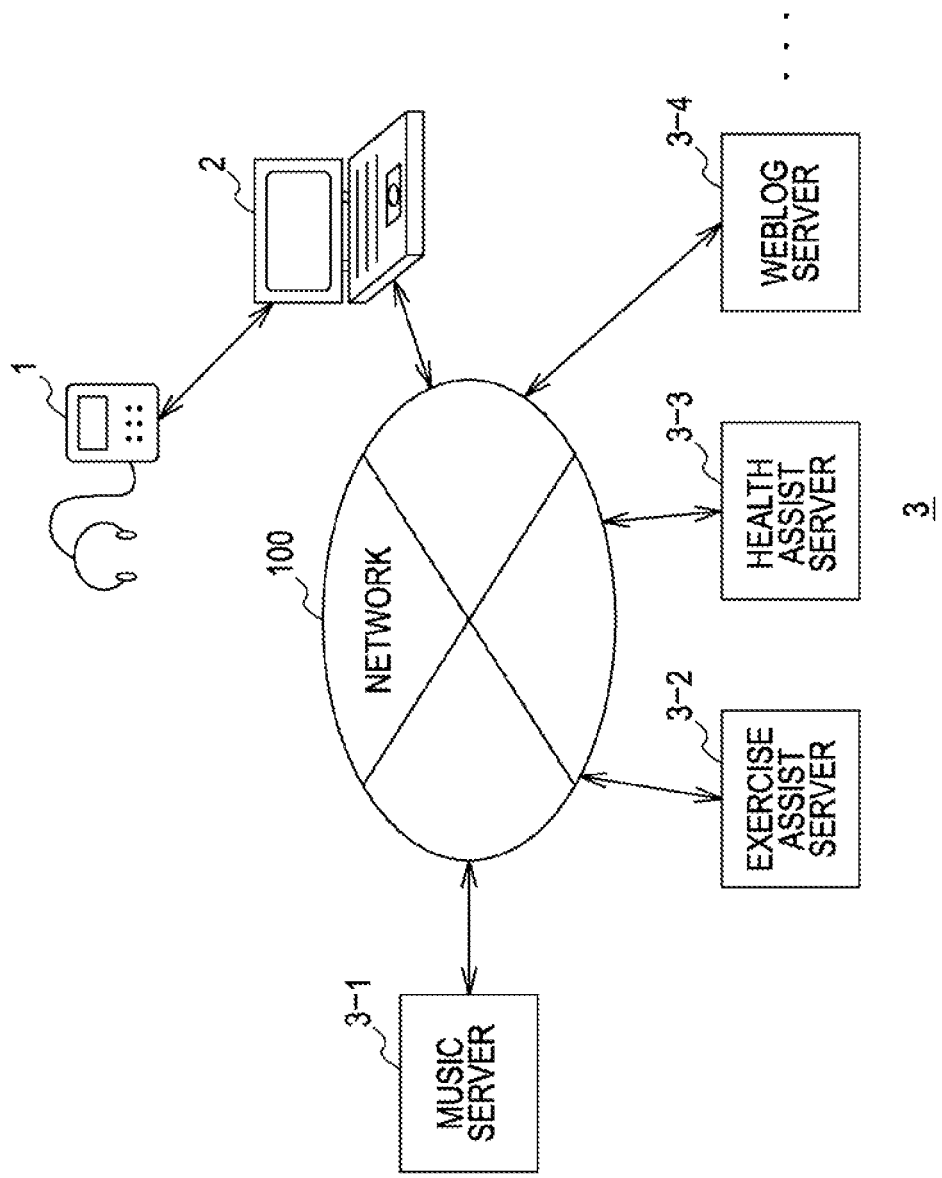
FIG. 1 is a diagram illustrating a health exercise assist system according to an embodiment of the present invention.

First, an overview of a health exercise assist system according to an embodiment of the present invention is described below. FIG. 1 is a diagram illustrating an overview of the health exercise assist system according to the present embodiment. This health exercise assist system is an implementation of a system, an apparatus, and a method according to the present invention. As shown in FIG. 1, the health exercise assist system according to the present embodiment includes a portable audio playback apparatus (a portable music playback apparatus) 1, an information processing apparatus 2, and one or more service information providing apparatuses 3 provided on a wide-area network such as the Internet 100.

The portable audio playback apparatus (hereinafter referred to simply as the audio playback apparatus) 1 is implemented to be small in size and weight so that a user can use it while carrying it by putting it in a pocket of a clothes or wearing it on pants with a belt or on an arm or the like with a dedicated holder.

The user of the audio playback apparatus 1 is allowed to perform various kinds of exercises such as walking, jogging, running, etc. while listening to music, via a headphone or an earphone, played back by the audio playback apparatus 1. The audio playback apparatus 1 is also capable of accepting an exercise plan indicating a target amount of exercise to be performed, as will be described in further detail later.

The audio playback apparatus 1 detects exercise information indicating a tempo or the like of an exercise performed by the user and stores the detected exercise information. The audio playback apparatus 1 is also capable of storing history information in terms of music played. The audio playback apparatus 1 detects the amount of exercise on the basis of the exercise information and plays music in accordance with the music data history information for a period until the target amount of exercise indicated by the exercise plan is achieved.

In the present embodiment, the audio playback apparatus 1 is capable of transmitting/receiving information to/from the information processing apparatus 2 via a digital interface such as a USB (Universal Serial Bus) bus or an IEEE (Institute of Electrical and Electronics Engineers) 1394 bus, an infrared interface according to the IrDA (Infrared Data Association) standard, a near-filed wireless communication interface such as a Bluetooth interface, a wireless communication interface using an RF (Radio Frequency) signal, an analog interface, or a storage medium such as a memory card.

The audio playback apparatus 1 can be connected to the information processing apparatus 2 via one of the interfaces described above whereby part or all of information including the history of the exercise information, the music data playback history information, and the preset target amount of exercise (exercise plan) is provided from the audio playback apparatus 1 to the information processing apparatus 2.

The information processing apparatus 2 is, for example, a personal computer installed in the home of the user of the audio playback apparatus 1, and has, as with the audio playback apparatus 1, a digital interface such as a USB bus interface or an IEEE 1394 bus interface, an infrared interface according to the IrDA standard, a near-filed wireless communication interface such as a Bluetooth interface, a wireless communication interface using an RF signal, an analog interface, and/or a storage medium interface such as a memory card interface, so that data can be transmitted/received to/from the audio playback apparatus 1 via one of these interface.

The information processing apparatus 2 has a communication capability that allows it to transmit a request for information to a service information providing apparatus 3 via a wide-area network such as the Internet 100 and to receive information transmitted from the service information providing apparatus 3 in response to the request.

A wide variety service information providing apparatuses can be available on the wide-area network 100. In the example shown in FIG. 1, service information providing apparatuses 3 on the wide-area network 100 include a music server 3-1, an exercise assist server 3-2, a health assist server 3-3, and a weblog server 3-4. Hereinafter, these servers will be generically referred to as service information providing apparatuses 3.

Each of the service information providing apparatus 3 disposed on the wide-area network 100 is capable of providing information to the information processing apparatus 2 in accordance with a request issued by the information processing apparatus 2. If necessary, the service information providing apparatus 3 produces service information in response to a request. That is, service information providing apparatuses 3 include a content server which provides various kinds of content data for free or at a fee, and an information providing server which provides various kinds of information for free or at a fee.

In the health exercise assist system according to the present embodiment, when a user of the audio playback apparatus 1 exercises while listening to music played by the audio playback apparatus 1, the audio playback apparatus 1 detects the amount of exercise performed, or the audio playback apparatus 1 captures information, from which to detect the amount of exercise performed by the user, such as exercise information indicating the exercise tempo or music data playback history information, and transmits the captured information to the information processing apparatus 2.

In accordance with the information supplied from the audio playback apparatus 1, the information processing apparatus 2 detects the amount of exercise performed by the user. The information processing apparatus 2 produces a service request including information indicating the amount of exercise performed by the user and identification information identifying the user of the audio playback apparatus 1, and the information processing apparatus 2 transmits the service request, using the communication capability, to a particular one of the service information providing apparatuses 3 on the wide-area network 100.

Note that the service request also includes information necessary to perform communication between the particular service information providing apparatus and the information processing apparatus 2, such as address information identifying the particular service information providing apparatus which is a destination of the service request, and address information identifying the information processing apparatus 2 which is a sender of the service request. In the present embodiment, the address information identifying the information processing apparatus 2 and that identifying the destination are stored in advance in a storage unit such as a memory disposed in the information processing apparatus 2.

If the service information providing apparatus 3 receives the service request, the service information providing apparatus 3 extracts exercise information associated with the user and detects the current and cumulative amounts of exercise performed by the user of the audio playback apparatus 1. The service information providing apparatus 3 then produces service information in accordance with the detected information and returns the produced service information to the information processing apparatus 2 which is the sender of the request.

If the information processing apparatus 2 receives the service information from the service information providing apparatus 3, the information processing apparatus 2 outputs the received service information to provide it to the user of the information processing apparatus 2, which is also the user of the audio playback apparatus 1.

As described above, the service information provided by the service information providing apparatus 3 is produced depending on the current and/or cumulative amount of exercise performed by the user of the audio playback apparatus 1, and thus the service information provided can vary with increasing amount of exercise. In other words, to receive new service information provided when a particular amount of exercise is achieved, the user of the audio playback apparatus 1 has to continue the exercise while listening to music played by the audio playback apparatus 1 until the particular amount of exercise is reached. This motivates the user of the audio playback apparatus 1 to continue the exercise while listening to music played by the audio playback apparatus 1.

That is, acquisition of useful service information by continuing exercise while listening to music played by the audio playback apparatus 1 motivates the user to continue everyday exercise for a long period.

Next, the configuration and the operation of each apparatus in the health exercise assist system according to the present embodiment are described in detail below.

Portable Audio Playback Apparatus

First, the audio playback apparatus 1 in the health exercise assist system according to the present embodiment is described in detail below. FIG. 2 is a block diagram illustrating the audio playback apparatus 1 according to the present embodiment. As described above, the audio playback apparatus 1 according to the present embodiment is of the portable type with a small size and a small weight, and is designed to be used in a state in which the audio playback apparatus 1 is put in a pocket of clothes. A user of the audio playback apparatus 1 can perform an exercise such as walking, jogging, or running while listening to music played by the audio playback apparatus 1.

As shown in FIG. 2, the audio playback apparatus 1 according to the present embodiment includes a control unit 10, a music information storage unit 21, a music playback data generator 22, an exercise information analysis circuit 23, an exercise information sensor 24, an audio signal output processing unit 31, a speaker 32, a display circuit 33, a display 34, a key operation unit 41, a microphone 42, an audio signal input processing unit 43, an external terminal 51, an interface (I/F) 52, and a storage device 53.

The control unit 10 is responsible for controlling various parts of the audio playback apparatus 1, and includes a CPU (Central Processing Unit) 11, a ROM (Read Only Memory) 12, and a RAM (Random Access Memory) 13, which are connected to each other via a CPU bus 14. The CPU 11 is a main part responsible for the control operation, and is adapted to execute a program and supply control signals generated in the execution of the program to various parts of the audio playback apparatus 1 thereby controlling the various parts. The ROM 12 stores various programs executed by the CPU 11 and various data used in the execution of programs. The RAM 13 is mainly used as a work area for temporarily storing intermediate results of the like.

The music information storage unit 21 is a part adapted to read or store music data from or into a storage medium. Various types of storage media can be used for this purpose. Specific examples include a hard disk, a magneto-optical disk such as a MD (Mini Disc (trademark)) disk, an optical disk such as a CD (Compact Disc) disk or a DVD (Digital Versatile Disc) disk, a semiconductor memory, an IC card memory using a semiconductor memory, and a magnetic tape. When a hard disk is used as the storage medium, the music information storage unit 21 is implemented by a hard disk drive. When an optical disk is used as the storage medium, the music information storage unit 21 is implemented by an optical disk drive.

The music playback data generator 22 performs various processes associated with music data to be played, under the control of the control unit 10. More specifically, as will be described later, the music playback data generator 22 selects music data to be played from a plurality of music data stored in the music information storage unit 21 and determines the order in which to play the selected music data.

The exercise information analysis circuit 23 analyzes an exercise performed by a user, under the control of the control unit 10. More specifically, as will be described later, the exercise information analysis circuit 23 calculates the amount of exercise performed by the user in synchronization with music provided by playing back music data, on the basis of personal profile information indicating the height, the weight and the sex of the user input via the key operation unit 41, and the attribute information indicating the playback time, the tempo, etc. of the music data played.

The exercise information analysis circuit 23 also has the capability of calculating the strength of exercise and the exercise time (exercise duration time) for which to perform exercise to achieve a target amount of exercise input via the key operation unit 41. The exercise information analysis circuit 23 is also capable of calculating the amount of exercise actually performed by the user, on the basis of a detection signal output from the exercise information sensor 24.

Note that the music playback data generator 22 and the exercise information analysis circuit 23, each of which is in a double line block in FIG. 2, may be implemented by executing a program by the control unit 10. That is, the functions of the music playback data generator 22 and the exercise information analysis circuit 23 may be implemented by an operation of the control unit 10.

The exercise information sensor 24 is implemented by a combination of one or more of the following sensors, an acceleration sensor, a shock sensor, a pressure sensor, an electrostatic voltage sensor, a strain gauge, a distance sensor, a current sensor, and a temperature sensor. The exercise information sensor 24 detects motion of the user and/or the temperate or the pulse rate of the user. The detection signal output from the exercise information sensor 24 is supplied to the exercise information analysis circuit 23, which calculates the amount of exercise actually performed by the user on the basis of the supplied information as described above.

In the present embodiment, the exercise information sensor 24 may be implemented, for example, by a three-axis acceleration sensor so that a moving tempo of walking or jogging is detected by analyzing a signal output from the acceleration sensor. Furthermore, by analyzing the signal output from the acceleration sensor used as the exercise information sensor 24, it is possible to determine the type of the exercise performed by the user. For example, it is possible to determine whether the user is walking or jogging.

In the audio playback apparatus 1 according to the present embodiment, the audio signal output processing unit 31 receives audio data (in digital form) to be played from the control unit 10 and performs processing including a digital-to-analog conversion on the received audio data to produce an analog audio signal to be output. The analog audio signal output from the audio signal output processing unit 31 is supplied to a speaker 32. The speaker 32 emits a sound/voice in accordance with the received analog audio signal.

The audio signal output processing unit 31 is connected to an audio output terminal (not shown). When a headphone or an earphone is connected to the audio output terminal, analog audio signal output from the audio signal output processing unit 31 is supplied to the headphone or the earphone via the audio output terminal so that a user is allowed to listen to a playback sound/voice emitted from the headphone or the earphone. In the state in which the headphone or the earphone is connected to the audio output terminal, no sound/voice is emitted from the speaker 32.

The display circuit 33 operates under the control of the control unit 10 to generate an image to be displayed on the screen of the display 34. The display 34 is implemented by a display device such as an LCD (Liquid Crystal Display) or an EL (Electro Luminescence) panel having a relatively large display screen on which to display various kinds of information. Under the control of the control unit 10, various kinds of text information and image information such as operation guidance, an error message, a title of music played, etc. are displayed on the screen of the display 34.

The key operation unit 41 includes a plurality of operation keys and function keys whereby a user is allowed to input a command or information to the audio playback apparatus 1. More specifically, for example, the user is allowed to input a music playback start/end command, select music to be played, input personal profile information, input a target value of exercise, etc. The microphone 42 senses a sound/voice and converts it into an electric signal. The resultant analog audio signal output from the microphone 42 is supplied to the audio signal input processing nit 43 and is subjected to a process including an analog-to-digital conversion, whereby the original analog audio signal is converted into a form that allows the audio signal to be stored in the storage medium of the music information storage unit 21 via the control unit 10.

The external terminal (the external input/output terminal) 51 functions as a terminal for connecting to an external device. For example, audio data output from another audio playback apparatus is input to the audio playback apparatus 1 via this external terminal 51, or music data is output from the audio playback apparatus 1 according to the present embodiment to an external device via the external terminal 51. The data type is not limited to music data, but programs or other various types of data may be input/output via the external terminal 51. The external terminal 51 of the audio playback apparatus 1 according to the present embodiment also functions as a terminal for connecting to the information processing apparatus 2 described later.

In the present embodiment, the data input via the external terminal 51 is captured by the I/F 52 in the audio playback apparatus 1 and is converted into a form that can be handled by the audio playback apparatus 1. Conversely, when data is output to an external device, the data is converted by the I/F 52 into a form that can be handled by the external device.

The storage device 53 is adapted to, as will be described in further detail later, store various kinds of information associated with main data to be stored. Specific examples of such information stored in this storage device 53 include identification information identifying music data played, characteristic information associated with the music data, personal profile information of a user, information indicating a calculated amount of exercise, etc. As a matter of course, main music data itself may be stored in this storage device 53.

Note that the storage device 53 is adapted to, as with the music information storage unit 21 described above, read/store various kinds of data from/into a storage medium. Various types of storage media can be used for this purpose. Specific examples include a hard disk, a magneto-optical disk such as a MD (Mini Disc (trademark)) disk, an optical disk such as a CD (Compact Disc) disk or a DVD (Digital Versatile Disc) disk, a semiconductor memory, an IC card memory using a semiconductor memory, a magnetic tape. When a hard disk is used as the storage medium, the storage device 53 is implemented by a hard disk drive. When an optical disk is used as the storage medium, the storage device 53 is implemented by an optical disk drive.

In accordance with a command input by a user via the key operation unit 41, the control unit 10 controls various parts to store, in the storage medium of the music information storage unit 21, music data supplied via the external terminal 51 and the I/F 51 and associated attribute information indicating the total playback time, the tempo, the genre, the music style, etc.

The control unit 10 produces a list of music stored as music data in the music information storage unit 21, and displays the list on the display screen of the display 34 via the display circuit 33. If a user selects one of music data from the list displayed on the display 34 by operating the key operation unit 41, the selected music data is played.

In the above process, in accordance with the playback command including selection information indicating music data to be played, input via the key operation unit 41, the control unit 10 reads the specified music data from the music information storage unit 21 and supplies the read music data to the audio signal output processing unit 31. As described above, an analog audio signal is produced by the audio signal output processing unit 31 from the supplied audio data, and a sound/voice is output in accordance with the analog audio signal from the speaker 32 or the headphone or the earphone connected to the external output terminal (not shown) so that the user can listen to the music.

In the audio playback apparatus 1, according to the present embodiment, the user is allowed to input personal profile information indicating the weight, the height, the sex, the age, etc. of the user via the key operation unit 41. It is also possible to input a target value of exercise to be performed (an exercise plan) via the key operation unit 41.

In the state in which the audio playback apparatus 1 has the personal profile information input in the above-described manner, when music data is played back, the exercise information analysis circuit 23 calculates the amount of exercise which will be achieved if the exercise is performed in synchronization with the music played back, in accordance with the personal profile information and the attribute information indicating the playback time, the tempo, etc. of the music played back.

The control unit 10 controls various parts to sequentially select music data and play the selected music data until the amount of exercise performed by the user reaches the input target value of exercise, thereby assisting the user of the audio playback apparatus 1 according to the present embodiment to continue the exercise until the target value of exercise is achieved.

Furthermore, in the audio playback apparatus 1 according to the present embodiment, when playback of music data is ended, information of the amount of exercise calculated by the exercise information analysis circuit 23 is displayed on the display 34 via the display circuit 33 so that the user can know the amount of exercise performed. Thus, the exact amount of exercise performed by the user is calculated easily and shown to the user, whereby the user can know how much exercise is performed when exercise is performed in synchronization with music played by the audio playback apparatus 1 and thus the user can know how much exercise the user should perform to achieve the goal. This motivates the user to continue the exercise.

In the present embodiment, if the exercise information sensor 24 included in the audio playback apparatus 1 detects exercise performed by the user, a detection signal is output from the exercise information sensor 24 and supplied to the exercise information analysis circuit 23. The exercise information analysis circuit 23 can calculate the amount of exercise actually performed by the user, on the basis of the received detection signal. The amount of actually performed exercise may also be displayed on the display screen of the display 34 so that the user can know it.

When exercise is performed, information associated with the exercise performed is stored in the storage device 53. The information stored includes the personal profile information, the target amount of exercise, the history of exercise information indicating the moving tempo or the like detected by the exercise information sensor 24, the identification information such as a title of music identifying the music played, the playback history in terms of the playback time, the number of times the music has been played, the playback tempo, etc.

The history information stored in the above described manner is transmitted to a particular one of the service information providing apparatuses 3 on the wide-area network 100 via the information processing apparatus 2 so that the user can receive service information via the service information providing apparatus 3 depending on the cumulative total amount of exercise, This motivates the user to continue the exercise for a long period such as one week, two week, one month, two months, and so on. That is, in cooperation with the information processing apparatus 2 and the service information providing apparatus 3, the audio playback apparatus 1 manages the amount of exercise so that the user can continue the exercise for a long period.

External Structure of Audio Playback Apparatus

Figure 3A:
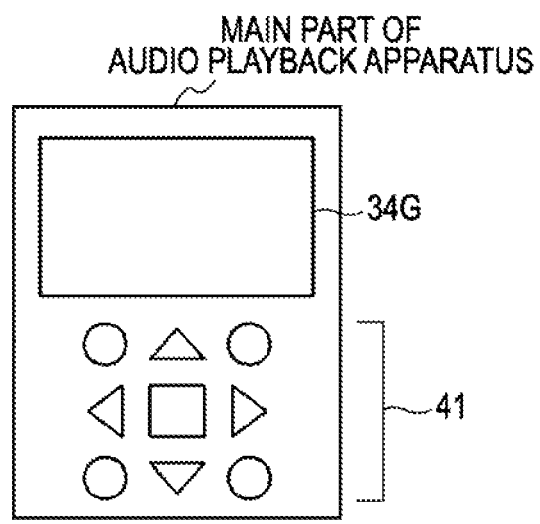
FIG. 3 is a diagram illustrating a typical appearance of an audio playback apparatus.
Figure 3B:
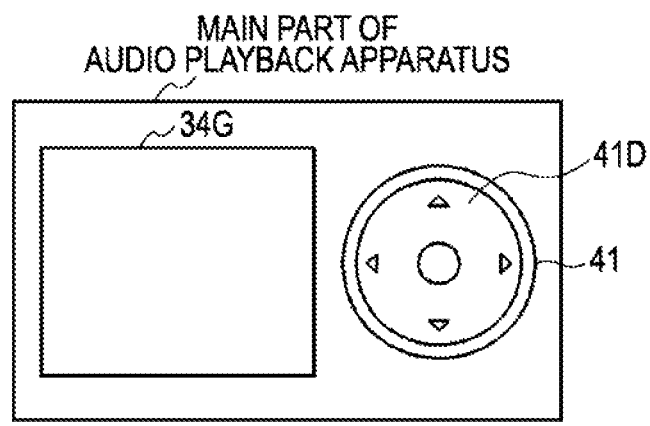
Figure 3C:
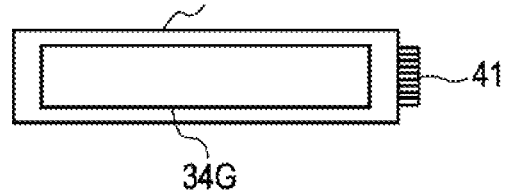

Next, typical examples of the external structure of the audio playback apparatus 1 according to the present embodiment are described. FIGS. 3A to 3C illustrate three typical examples of the external structure of the audio playback apparatus 1 according to the present embodiment. In the present embodiment, the external size of the audio playback apparatus 1 is determined to be small enough to be put in a breast pocket of a user or small enough to be held in a hand.

More specifically, in the greatest case, as shown in FIGS. 3A and 3B, the size of the audio playback apparatus 1 according to the present embodiment is small enough to be put in a breast pocket of a user. In a smaller case, as shown in FIG. 3C, the audio playback apparatus 1 has a size similar to the total size of a stack of several pieces of plate-shaped chewing gum. The external size or the weight may be further smaller as required.

FIGS. 3A and 3B illustrate two examples of the external structure of the audio playback apparatus 1 configured to be small enough to be put in a breast pocket of a user. In the example shown in FIG. 3A, the audio playback apparatus 1 is used in a position in which a longitudinal direction of the audio playback apparatus 1 is in a vertical direction. In the example shown in FIG. 3B, the audio playback apparatus 1 is used in a position in which the longitudinal direction of the audio playback apparatus 1 is in a horizontal direction.

In the examples shown in FIGS. 3A and 3B, a display screen of a display such as a LCD display and a key operation unit are disposed on a front surface (facing a user) of the audio playback apparatus 1. In the case of the vertical-type audio playback apparatus 1 shown in FIG. 3A, the key operation unit 41 is disposed in an area below the display screen 34G. Alternatively, the display screen 34G and the key operation unit 41 may be disposed at locations vertically opposite to the locations in the example shown in FIG. 3A. Still alternatively, the display screen 34G may be disposed in a center area of the front surface of the audio playback apparatus 1, and part of the key operation unit 41 may be disposed in an area above the display screen 34G and the remaining part of the key operation unit 41 may be disposed in an area below the display screen 34G.

In the case of the horizontal-type audio playback apparatus 1 shown in FIG. 3B, the key operation unit 41 is disposed in an area horizontally adjacent to the display screen 34G. The display screen 34G and the key operation unit 41 may be disposed at locations horizontally opposite to the locations in the example shown in FIG. 3B. That is, one of the display screen 34G and the key operation unit 41 is disposed in an area on the right-hand side, and the other is disposed on the left-hand side. Alternatively, the display screen 34G may be disposed in a center area of the front surface of the audio playback apparatus 1, and part of the key operation unit 41 may be disposed in an area left to the display screen 34G and the remaining part of the key operation unit 41 may be disposed in an area right to the display screen 34G.

In the example shown in FIG. 3A, the key operation unit 41 is configured using only button keys which are pressed in operation. In the example shown in FIG. 3B, the key operation unit 41 is configured in the form of a dial 41D which is operable by sliding a finger on the surface thereof and which is also operable by pressing particular parts thereof. The dial 41D may be configured, instead of to be operable by sliding a finger on the surface thereof, to be mechanically rotatable.

When the audio playback apparatus 1 is configured to be very small in size, as is the case with the example shown in FIG. 3C, it is difficult to dispose a key operation unit 41 on the front surface of the audio playback apparatus 1 in a similar manner to the example shown in FIG. 3A or 3B. Thus, in the example shown in FIG. 3C, a key operation unit 41 configured in the form of a rotatable dial key is disposed on an end face of the audio playback apparatus 1.

The key operation unit 41 may be configured in the form of a jog dial operable by rotating and pressing it, or in the form of an operation lever such as a joystick. When the display screen 34G of the display of the audio playback apparatus 1 is rather large as is the case with the examples shown in FIGS. 3A and 3B, a touch panel may be attached to the display screen 34G such that the key operation unit 41 is operable by a combination of the touch panel and information displayed on the display screen 34G.

By using the key operation unit 41 configured in one of forms described above with reference to FIGS. 3A to 3C, a user is allowed to input various kinds of information such as text information indicating a name of the user or the like, numerals, and/or symbols, and is allowed to select an item by moving a cursor. A plurality of characters may be assigned to each button key so that characters can be input using a small number of button keys. When a dial key is used, a character is temporarily selected by sliding a finder on the surface of the dial or by rotating the dial, and the temporarily selected character is finally selected by pressing a particular button key or the dial it self.

Note that the external structure and the configuration of the operation unit are not limited to those shown in the FIGS. 3A to 3C, but the audio playback apparatus 1 may be configured in many ways in size and shape. The key operation unit is also not limited to the types shown in FIGS. 3A and 3B. For example, in the structure in the example shown in FIG. 3A or in the example shown in FIG. 3B, a dial, a jog dial, and/or one or more button keys ma be additionally disposed on one or more side faces. That is, the key operation unit may be configured in a wide variety of combinations of button keys, a dial, a jog dial, a touch panel, a joystick, a slidable operation switch, etc.

Operation of Audio Playback Apparatus

The operation of the audio playback apparatus 1 according to the present embodiment is described below with reference to flow charts shown in FIGS. 4 and 5. In the following description, FIGS. 6A and 6B illustrating an example of a manner of inputting personal profile information, FIGS. 7A, 7B, 8A, and 8B illustrating examples of manners of inputting a target amount of exercise, FIG. 9 illustrating an example of a list of playable music, FIGS. 10A and 10B illustrating examples of playlists, FIG. 11 illustrating an example of information displayed on the display screen when music is being played, FIG. 12 illustrating an example of information of an amount of exercise and associated information displayed on the display screen, and FIGS. 13A and 13B illustrating examples of history information are also referred to as required.

Figure 4:
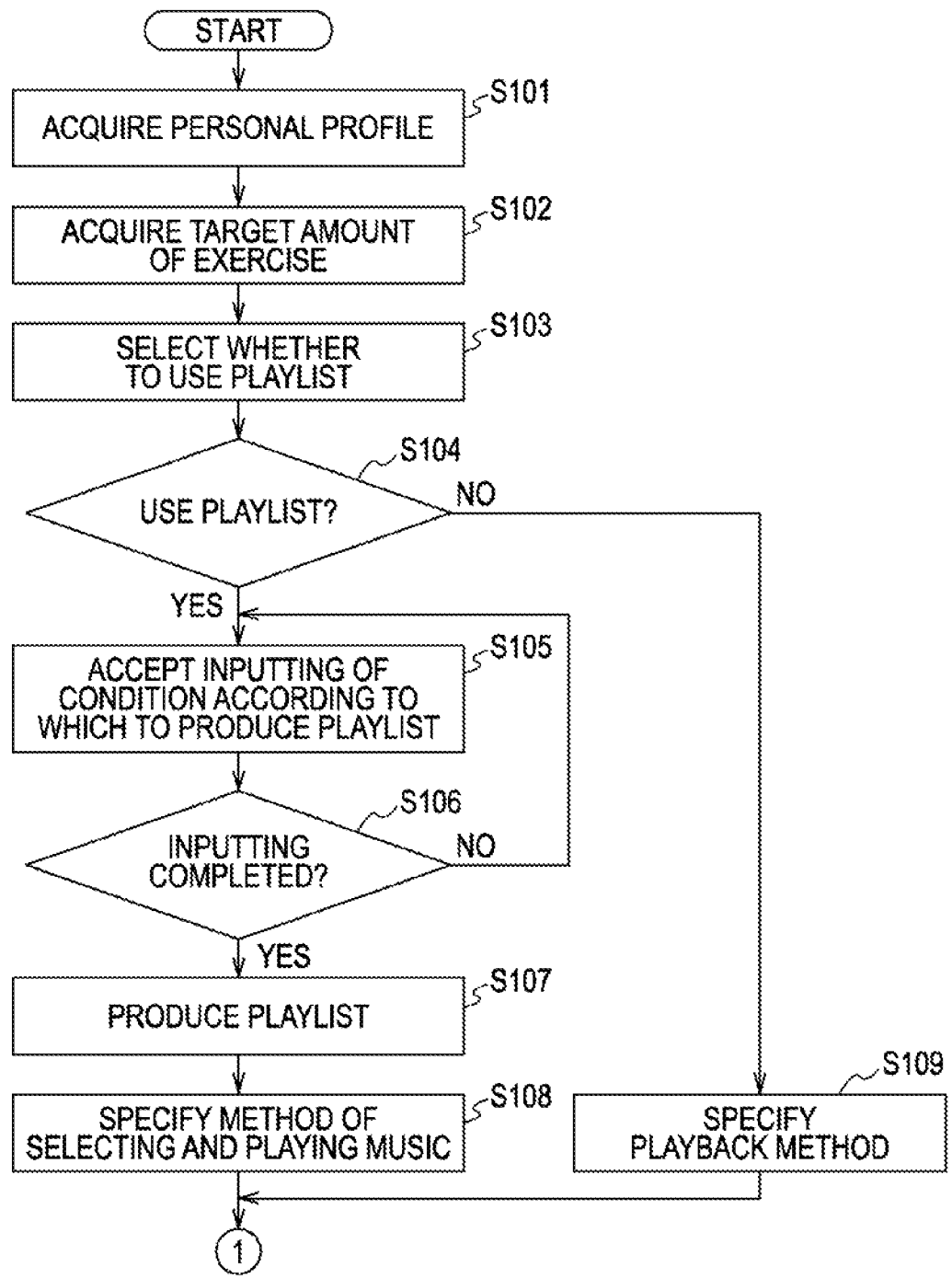
FIG. 4 is a part of a flow chart illustrating an operation of an audio playback apparatus.
Figure 5:
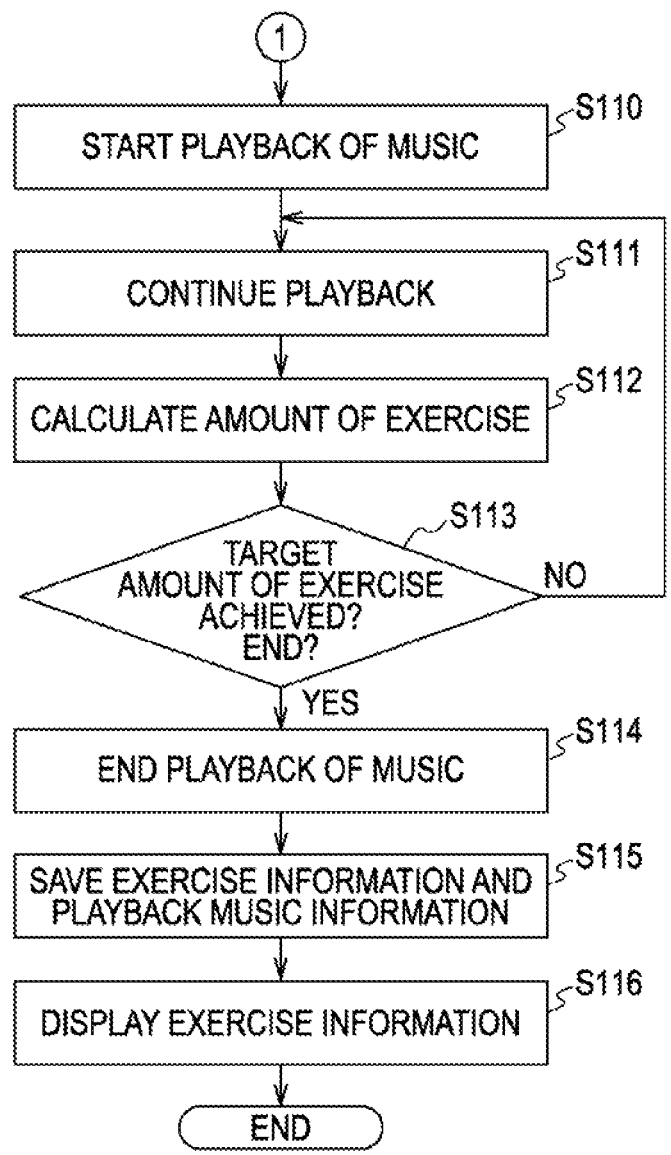
FIG. 5 is a part, following the part shown in FIG. 4, of the flow chart illustrating the operation of the audio playback apparatus.

FIGS. 4 and 5 are flow charts illustrating a process performed by the audio playback apparatus 1 according to the present embodiment to play music so that a user is allowed to listen to the music while exercising. When a user of the audio playback apparatus 1 turns on the power of the audio playback apparatus 1 with the intention of performing an exercise such as walking or jogging while listening to music played by the audio playback apparatus 1 according to the present embodiment, the control unit 10 of the audio playback apparatus 1 starts the process shown in FIGS. 4 and 5. First, in the process, personal profile information input by the user is acquired (step S101).

In this step S101, a screen such as that shown in FIG. 6A is displayed so that the user is allowed to input personal profile information by operating the key operation unit 41. In this example, as shown in FIG. 6A, the name, the sex, the age, the height, the weight, etc. of the user, which are necessary to calculate the amount of exercise, are input as the personal profile information.

If the control unit 10 acquires the personal profile information, then, as shown in FIG. 6B, the control unit 10 displays the name, the sex, the age, the height, and the weight of the user, and also the BMI (which is an abbreviation for "body mass index" and which is given by the weight (kg)÷the square of the height (m)) calculated from the height and the weight of the user, and the obesity level, on the display screen 34G of the display 34. If information displayed is correct, the user presses a YES button, but otherwise the user presses a NO button. If the NO button is pressed, the input screen shown in FIG. 6A is displayed again so that the user is allowed to make a correction. Note that in the flow chart shown in FIG. 4, step S101 includes a process of making a correction of personal profile information.

Next, the control unit 10 acquires a target amount of exercise via an inputting operation performed by the user (step S102). In this step S102, for example, an input screen such as that shown in FIG. 7A is displayed to prompt the user to input a target amount of exercise. More specifically, in the example shown in FIG. 7A, a length of time for which the user plans to perform exercise such as walking or jogging at a time, and calories to be consumed by the exercise are input.

If the control unit 10 acquires the target amount of exercise, then the control unit 10 displays the acquired target amount of exercise and the target value of energy to be consumed on the display screen 34G of the display 34, as shown in FIG. 7B. If information displayed is correct, the user presses a YES button, but otherwise the user presses a NO button. If the NO button is pressed, the input screen shown in FIG. 7A is displayed again so that the user is allowed to make a correction.

The screen for inputting the target amount of exercise is not limited to that shown in FIG. 7A or 7B. For example, a screen shown in FIG. 8A may be displayed to prompt the user to input an exercise type and an exercise time for each of one or more exercise types. For example, one or a combination of walking, jogging, running etc. may be input as exercise types, and an exercise time for each exercise type may be input. If the user wants to input values for a further exercise type, the user presses an ADD button, but otherwise the user presses an END button.

If the ADD button is pressed, the control unit 10 further acquires an exercise type and an exercise time. Thus, the user is allowed to specify details of a sequence of exercise. For example, the sequence of exercise may be specified to include jogging for 5 minutes as warming-up exercise, running for 20 minutes, and jogging for 5 minutes as cooling-down exercise.

If the END button on the input screen shown in FIG. 8A is pressed, the control unit 10 displays, as shown in FIG. 8B, the input exercise types and exercise times on the display screen 34G of the display 34 for all exercise types input via the input screen shown in FIG. 8A. If information displayed is correct, the user presses a YES button, but otherwise the user presses a NO button. If the NO button is pressed, the input screen shown in FIG. 8A is displayed again so that the user is allowed to make a correction.

As described above, target amounts of exercise may be input in various manners in step S102. For example, an input screen may be switched in accordance with a selection made by a user so that a target exercise time and a target calorie value to be consumed are input as shown in FIG. 7A, or exercise types and exercise times are input as shown in FIG. 8A.

That is, the step S102 in FIG. 4 includes the process of selecting an input screen, inputting exercise types and exercise times, and making a correction.

Next, the control unit 10 controls the display circuit 33 to display, on the display screen 34G of the display 34, a guidance message prompting the user to select whether to use a playlist. The user makes a selection via the key operation unit 41 as to whether to use a playlist in playback of music (step S103).

That is, the audio playback apparatus 1 according to the present embodiment has two modes. In one mode, a playlist of music to be played is produced in accordance with selections made by a user, and music is played in accordance with the playlist. In the other mode, music is played without using a playlist.

Thus, in step S103, a selection is made as to whether to use the playlist, and then in step S104, a determination is made as to whether use of the playlist is selected. If it is determined in step S104 that use of the playlist is selected, the control unit 10 controls the display circuit 33 to display, on the display screen 34G of the display 34, a guidance message to prompt the user to specify a condition according to which to produce the playlist. In response to the guidance message, the user specifies via the key operation unit 41 the condition according to which to produce the playlist (step S105).

More specifically, in this step S105, as will be described in further detail later, it is specified to produce the playlist so as to include, for example, a plurality of pieces of music which are similar in tempo, which are composed/played by the same artist, or which are similar in genre. The control unit 10 then determines whether inputting associated with the condition according to which to produce the playlist is completed (step S106).

If it is determined in step S106 that the inputting is not yet completed, the control unit 10 returns the processing flow to step S105 to allow the user to input a condition according to which to produce the playlist. If it is determined in step S106 that the inputting is completed, the control unit 10 selects one or more pieces of music data meeting the specified condition from music data playable by the audio playback apparatus 1, in accordance with the condition specified in step S105 (step S107).

In the audio playback apparatus 1 according to the present embodiment, a large number of pieces of music data playable by the audio playback apparatus 1 and a list (a music information list) of playable music data such as that shown in FIG. 9 are stored in the storage medium of the music information storage unit 21. Note that music data are managed by using this music information list.

In the audio playback apparatus 1 according to the present embodiment, the music information list stored in the storage medium of the music information storage unit 21 includes, as shown in FIG. 9, a music title, a tempo, a length (a play time), a genre, and a performer (artist) for each piece of music data playable by the audio playback apparatus 1. The playlist is produced on the basis of this music information list. A list of playable music may be displayed, in accordance with the music information list, on the display screen 34G of the display 34 via the display circuit 33 so that the user is allowed to select music data to be played.

In step S107, the control unit 10 selects music data from the music information list shown in FIG. 9, in accordance with the condition specified in step S105, and produces the playlist. For example, in a case where the condition specifies that the playlist should include a plurality of pieces of music with a tempo of 81±1 BPM, pieces of music data with a tempo of 80, 81, or 82 are selected from the music information list shown in FIG. 9 and a playlist including these selected pieces of music is produced as shown in FIG. 10A. In a case where it is specified that the playlist should include a plurality of pieces of music whose genre is POP, pieces of music data whose genre is POP are selected from the music information list shown in FIG. 9 and a playlist including these selected pieces of music is produced as shown in FIG. 10B.

After the playlist is produced, the control unit 10 controls the display circuit 33 to display, on the display screen 34G of the display 34, a guidance message to prompt the user to specify a method of selecting and playing music. In response to the message, the user specifies, via the key operation unit 41, the method of selecting and playing music (step S108).

In this step S108, more specifically, it is specified to sequentially play music in the same order as the order described in the playlist or play music in a random order. It is also allowed to specify the number of times each piece of music should be played, and to select particular pieces of music to be actually played (or not to be played) from the playlist. After step S108, the processing flow proceeds to step S110 in FIG. 5.

On the other hand, in a case where it is determined in step S104 that the selection is made so as to not use the playlist, the control unit 10 then prompts the user to specify how to play music without the playlist. The user specifies, for example, to play music data registered in the music information list in the same order as described in the music information list or in a random order, and also selects particular pieces of music to be played, from the music information list (step S109). After step S109, the processing flow proceeds to step S110 in FIG. 5.

In the audio playback apparatus 1 according to the present embodiment, the control unit 10 selects music data to be played and plays the selected music data in accordance with the playlist produced in step S107 and the playing method specified by the user in step S108 if use of the playlist is specified, or in accordance with the playing method specified by the user in step S109 if non-use of the playlist is specified (step S110).

In this step S110, as shown in FIG. 11, information associated with music data being played, such as a title, an artist (performer) name, a genre, a tempo, etc. of the music being played may be displayed on the display screen 34G of the display 34 to present the information to the user. Note that the information associated with the music data being played is produced on the basis of the music information list described above with reference to FIG. 9.

Although an exercise type and strength of exercise are also displayed in FIG. 11, these are actually calculated in a later step S112, and thus these are not actually displayed on the display screen 34G of the display 34 at the point of time when step S110 is performed.

Thereafter, the control unit 10 of the audio playback apparatus 1 according to the present embodiment continues selecting and playing music data as specified by the user (step S111) until it is determined in step S113 that the amount of exercise performed by the user has achieved the target value.

That is, in step S111, the process of playing music started in step S110 is continued such that each time playing of one piece of music is completed, a next piece of music is selected in accordance with the playlist produced in step S107 if use of the playlist is specified and the playing method specified by the user in step S108, or in accordance with the playing method specified by the user in step S109 if non-use of the playlist is specified, and the selected piece of music is played.

The control unit 10 of the audio playback apparatus 1 according to the present embodiment calculates the cumulative total amount of exercise on the basis of information obtained as a result of analysis by the exercise information analysis circuit 23 on exercise information detected by the exercise information sensor 24, taking into account the playback tempo and the playback time of each piece of music (step S112).

As described above, the exercise information sensor 24 of the audio playback apparatus 1 according to the present embodiment is implemented by the three-axis acceleration sensor whereby the exercise information analysis circuit 23 detects the moving tempo of the user by detecting the peak period of the detection signal (the waveform) output from the exercise information sensor 24. The period of the detection signal may be determined by calculating the autocorrelation of the detection signal or by performing frequency spectrum analysis on the detection signal. The moving tempo of the user may be detected by other methods.

The amount of exercise performed by the user, the walking (running) distance (or the moving distance), and the consumption energy can be calculated taking into account the detected moving tempo and the playback time of music as described above. Herein, the amount of exercise refers to the cumulative amount of exercise as counted from the start of the first-time exercise. To calculate such the cumulative value, the cumulative amount of exercise achieved in the last-time exercise is stored, and the amount of exercise calculated at predetermined intervals (such as every 5 or 10 seconds) in step S112 and the calculated value is added to the cumulative amount stored thereby updating the cumulative amount of exercise.

As described above with reference to FIG. 9, the music information list also includes information indicating the tempo of each piece of music. Therefore, instead of detecting the actual tempo of motion of the user, the tempo of music being played may be regarded as the tempo of the motion of the user, and the amount of exercise may be calculated based on the tempo of music.

In the present embodiment, on the basis of a vertical acceleration component of the acceleration detected by the three-axis acceleration sensor of the exercise information sensor 24, the type of exercise being performed by the user is determined in step S112. For example, it is determined whether the user is walking or jogging. It is known that jogging is two or three times greater in impact than walking. Thus, from the magnitude of the vertical component of the acceleration detected by the acceleration sensor, it is possible to determine at least whether the user is walking or jogging.

In the audio playback apparatus 1 according to the present embodiment, in step S112, a MET (Metabolic Equivalent) value indicating the strength of exercise performed by the user is determined on the basis of the calculated moving tempo and the exercise type. As will be described in detail later, the MET value is obtained by dividing the oxygen uptake during exercise, determined from the horizontal moving component and the vertical moving component, by the predetermined oxygen consumption in a resting state. It is possible to calculate energy consumed by the user by using the MET value.

The control unit 10 of the audio playback apparatus 1 according to the present embodiment determines whether the amount of exercise performed by the user, calculated in step S112, has reached the target amount of exercise specified in step S102 (step S113). If it is determined in step S113 that the calculated amount of exercise performed by the user has not yet reached the target amount of exercise, the process is repeated from step S111.

If it is determined in step S113 that the calculated amount of exercise performed by the user has reached the target amount of exercise, the control unit 10 of the audio playback apparatus 1 according to the present embodiment ends the playback of the music data by controlling various parts such as the music information storage unit 21, the music playback data generator 22, and the audio signal output processing unit 31 in the audio signal playback section of audio playback apparatus 1 (step S114).

Thereafter, the control unit 10 of the audio playback apparatus 1 stores, in the storage medium of the storage device 53, an exercise execution history including a history of exercise information and a music playback history, and an exercise plan history (step S115). FIGS. 13A and 13B illustrates examples of history information stored in step S115 in the storage medium of the storage device 53 of the audio playback apparatus 1.

FIG. 13A illustrates an example of an exercise plan history which is produced on the basis of the target amount of exercise input by the user in step S102 in FIG. 4. In the case where a target amount of exercise is set by inputting an exercise time and consumption energy in calories as shown in FIG. 7, information indicating a serial number identifying an individual exercise plan (indicating a target amount of exercise), information indicating date/time at which the exercise plan was made (expressed in a format of YY(year)MM(month)DD (day)HH(hours)MM(minutes) as in the example shown in FIG. 13A), information indicating an exercise time (expressed as 25 min in the example shown in FIG. 13A), and information indicating energy to be consumed (expressed as 770 cal in the example shown in FIG. 13A) are stored as the exercise plan history in the storage medium of the storage device 53, as shown in a lower part of FIG. 13A.

In the case where an exercise type and an exercise time are input as described above with reference to FIG. 8, information indicating a serial number identifying an individual exercise plan (indicating a target amount of exercise), information indicating date/time at which the exercise plan was made (expressed in a format of YY(year)MM(month)DD(day)HH (hours)MM(minutes) as in the example shown in FIG. 13A), and information indicating planned exercise types and planned exercise times (expressed as jogging 5 min+running 20 min+jogging 5 min in the example shown in FIG. 13A) are stored as the exercise plan history in the storage medium of the storage device 53, as shown in an upper part of FIG. 13A.

FIG. 13B illustrates an example of an exercise execution history. As shown in FIG. 13B, the exercise execution history includes information (playback music information) associated with music data played and information (exercise information) associated with exercises performed by a user. The information (playback music information) associated with music data includes a title, a tempo, and a play time of each piece of music, and the information (exercise information) associated with exercises performed by the user includes a running type (planned), an exercise tempo (average), a running type (detected), and the number of steps (calculated).

The exercise execution history is produced and stored separately as a history of a first-time exercise, a history of a second-time exercise, and so on each time the process shown in FIGS. 4 and 5 is performed. Each of individual exercise execution history sets such as the history of the first-time exercise, the history of the second-time exercise, and so on includes information (for example, date/time at which each history set was produced) identifying each history set.

The information indicating the date/time at which the history is produced may be produced as follows. A clock circuit (not shown) having a calendar function is connected to the control unit 10, and the control unit 10 acquires the current year, month, day of the moth, and day of the week from the clock circuit and describes the acquired information in the exercise execution history.

The playback music information is produced on the basis of the music information list shown in FIG. 9. Of the items of the exercise information, the running type (planned) corresponds to the target amount of exercise input in step S102, and the exercise tempo (average) is the average value of exercise tempos detected by the exercise information sensor 24 and the exercise information analysis circuit 23 during a period in which music data was played.

Of the items of the exercise information, the running type (detected) indicates a running type determined from the vertical component of the acceleration of the motion of the user detected by the exercise information sensor 24. More specifically, the running type (detected) indicates whether the user actually performed walking or jogging. The number of steps (calculated) is obtained by multiplying the play time and the exercise tempo (average).

In the exercise execution history shown in FIG. 13B, a description of a first-time execution indicates that the exercise was performed as follows. In a first phase planned to play music A with a tempo of 82 for 3 minutes for walking, 246 steps were actually walked at a moving tempo of 82. In a second phase planned to play music C with a tempo or 81 for 5 minutes 52 seconds for jogging, 481 steps were actually jogged at a moving tempo of 82. In a third phase planned to play music B with a tempo of 120 for 8 minutes for running, 936 steps were actually run at a moving tempo or 117. As described above, in the exercise history of the first-time execution, information indicating exercise actually performed by the user while listening to music is described for each piece of music.

The exercise time for which exercise was performed by the user can be determined from the play time. The amount of exercise and the consumed energy in calories can be calculated from the exercise time, the exercise type, and the number of steps.

In the example shown in FIG. 13B, the playback music information and the exercise information are recorded for each piece of music played. Alternatively, the playback music information and the exercise information may be recorded for each exercise type (running type), or may be recorded in predetermined intervals (for example, every 30 seconds, every 1 minute, every 2 minutes, every 3 minutes, etc.). It is desirable to record the music playback information and the exercise information for each piece of music played, as in the example shown in FIG. 13B, because this makes it easy to calculate the amount of exercise from the music playback information.

After the history information is stored in step S115 in the storage medium of the storage device 53 in the manner described above with reference to FIGS. 13A and 13B, the control unit 10 of the audio playback apparatus 1 displays information (exercise information) associated with exercise performed by the user this time on the display screen 34G of the display 34 via the display circuit 33 (step S116). Thus, the process shown in FIGS. 4 and 5 is completed.

More specifically, in step S116, the exercise time, the walking distance (moving distance), the average speed, the consumed energy in calories, the amount of burnt fat, etc. are calculated and displayed on the display screen 34G of the display 34, for example, in a form shown in FIG. 12.

In the audio playback apparatus 1 according to the present embodiment, as described above, the target amount of exercise is input by a user, music is played in accordance with a playing method specified by the user, and the amount of exercise performed by the user in synchronization with the music played is detected, thereby motivating the user to continue exercise until the amount of exercise actually performed by the user reaches the target amount of exercise.

Furthermore, in the present embodiment, as described above with reference to FIG. 13, the audio playback apparatus 1 produces the exercise plan history and the exercise execution history including playback music information and exercise information, and stores them. The history information produced in the above-described manner is sent to a particular server functioning as the service information providing apparatus via a personal computer or the liker serving as the information processing apparatus 2. Depending on the amount of exercise actually performed by the user, the service information providing apparatus provides service information to the audio playback apparatus 1 via the information processing apparatus 2.

In the process described above with reference to the flow charts shown in FIGS. 4 and 5, the audio playback apparatus 1 ends the music playing operation when the amount of exercise actually performed by the user reaches the target amount of exercise input in step S102. Alternatively, the determination process in step S113 may also include a process of determining whether the playing operation has been stopped, and the processing flow may proceed to step S114 when it is determined that the playing operation has been stopped. When the playing operation is forced to be stopped, the history information such as that shown in FIG. 13 is produced and stored in the storage medium of the storage device 53. In this case, the amount of exercise performed by the user may be displayed on the display screen 34G of the display 34 in a form similar to that shown in FIG. 12. Instead of making the additional determination in step S113, an additional step may be provided to make the determination as to whether the playing operation has been stopped, and the processing flow may proceed to step S114 when it is determined that the playing operation has been stopped.

Method of Calculating the Amount of Exercise

The process of calculating the amount of exercise in step S112 in FIG. 5 is described in further detail below. In step S112, as described above, a calculation is performed to determine the amount of exercise which is achieved when exercise is performed in a predetermined manner in synchronization with music played by the audio playback apparatus 1 according to the present embodiment. More specifically, in this calculation process, the amount of exercise performed by the user is estimated on the basis of the personal profile information indicating the weight, the height, the age, the sex, etc. input by the user and the attribute information indicating the play time and the tempo of music played or the average exercise tempo detected by the exercise information sensor 24.

The exercise time is assumed to be equal to the play time of music. The play time of music is measured and stored as part of the exercise execution history as shown in FIG. 13B. The exercise time for which the user performed exercise is given by the sum of play times of all pieces of music played.

The walking distance (the moving distance) is determined on the basis of the personal profile information and the attribute information of music played. FIG. 14 shows examples of calculations of the waking distance. It is known that the step size in walking is approximately equal to 45% of the height of the user as described in formula (1) in FIG. 14, and the step size in jogging is approximately equal to 50% of the height as described in formula (2) in FIG. 14. Thus, the walking distance is given by the step size depending on the type of exercise performed by the user times the number of steps as described in formula (3) in FIG. 14.

In a first example shown in FIG. 14, the walking distance is calculated for a case where a user with a height of 170 cm walks for 2 minutes 30 seconds in synchronization with music with a temp of 120. In this case, as described in formula (4), the step size is first calculated as the height times 0.45, and the step size is multiplied by the number of steps per minute, 120, which is determined by assuming that the number of steps per minute is equal to the number of beats per minute of music played thereby determining the walking distance per minute. The walking distance per minute is then multiplied by the exercise time (the exercise duration time) which is equal to 2 minutes 30 seconds in this specific example. Thus, the walking distance is determined as 229.5 m as described in (4) of FIG. 14.

In a second example shown in FIG. 14, the walking distance (the running distance) is calculated for a case where a user with a height of 170 cm runs (performs jogging) for 2 minutes 30 seconds in synchronization with music with a temp of 170. In this case, as described in formula (5), the step size is first calculated as the height times 0.5, and the step size is multiplied by the number of steps per minute, 170, which is determined by assuming that the number of steps per minute is equal to the number of beats per minute of music played thereby determining the walking distance (the moving distance) per minute. The walking distance (the moving distance) per minute is then multiplied by the exercise time (the exercise duration time) which is equal to 2 minutes 30 seconds in this specific example. Thus, the walking distance is determined as 361.24 m as described in (5) of FIG. 14.

In the examples described above, the tempo of music is used in the calculation. However, when the average exercise tempo actually performed by the user is detected by the exercise information sensor 24 and is described in the exercise execution history as in the example shown in FIG. 13B, the exercise tempo (the average exercise tempo) may be used instead of the tempo of music in the calculation of the walking distance. Herein, for simplicity, the moving distance is generically denoted by "walking distance" regardless of whether the exercise is walking or jogging, without distinguishing between walking and jogging.

The average speed in exercise can be determined from the exercise time and the walking distance, which can be determined in the above-described manner. FIG. 15 shows an example of a calculation of the average moving speed during exercise. The average speed is calculated by dividing the walking distance by the exercise time as described in formula (6) in FIG. 15. Thus, if a length of 3 km is walked for 30 minutes, then the average speed is calculated as 6 km/hour as described in (7) in FIG. 15.

Energy (in calories) consumed by exercise can be determined from consumed energy per minute or from the MET (Metabolic Equivalent) value indicating the strength of exercise determined for each exercise.

FIG. 16 shows an example of calculation of consumption energy based on consumption energy per minute. Consumption energy per minute, Wmin, is given by the sum of a constant 35 and the speed in exercise divided by the product of a constant 2000 and the weight of an exercising person, according to formula (8) in FIG. 16. The total energy consumed during exercise can be determined by multiplying the consumption energy per minute Wmin by the total exercise time (minutes).

In a specific example shown in FIG. 16, if a person with a weight of 68 kg walks at a speed of 100 m/min for 60 minutes, consumption energy is given by the consumption energy per minute Wmin determined according to formula (9) in FIG. 16 times the total exercise time according to formula (10) in FIG. 16. Thus, the consumption energy is determined as 275.4 kcal in this specific example.

FIG. 17 shows an example of calculation of consumption energy based on the MET value indicating the strength of exercise. In the audio playback apparatus 1 according to the present embodiment, the MET value is selected in step S112 in FIG. 5 from MET values predetermined for respective types of exercise. For example, as shown in FIG. 17, the MET value is 4 to 7 for walking, and 7 to 15 for jogging, if exercise is performed in an effective manner.

The consumption energy based on the MET value is given by the weight of the exercising person times the MET value times the exercise time according to formula (11) in FIG. 17. For example, if a person with a weight of 60 kg performs exercise with a MET value of 5 for 30 minutes, the consumption energy is calculated as 150 kcal as shown in (12) of FIG. 17.

For example, when music A with an MET value of 3.5, music B with an MET value of 5.0, music C with an MET value of 3.5, music D with an MET value of 3.0, music E with an MET value of 4.0, and music F with an MET value of 3.5 described in music information list shown in FIG. 9 are played sequentially, and a user with a weight of 60 kg exercises in synchronization with music played, the consumption energy is calculated as 82.095 kcal as shown in (13) of FIG. 17.

Note that in formula (13) in FIG. 17, a value 60 appearing first on the right-hand side is the weight of the user. The sum of products of play times and the strength of exercise (the MET values) for all pieces of music A to F is calculated in parentheses on the right-hand side in formula (13) in FIG. 17. The result is divided by 60 to convert the play time expressed in minutes to a value expressed in hours.

As described above, energy (in calories) consumed during exercise can be determined based on consumption energy per minute or based on an MET value indicating exercise strength determined for each type of exercise. Thus, as shown in FIGS. 16 and 17, the consumption energy can be determined using the weight of a user described in the personal profile information, and the exercise time (exercise duration time) assumed to be equal to the play time of music played by the audio playback apparatus 1 according to the present embodiment, or the speed calculated based on the exercise time.

The amount of fat burnt can be calculated using the consumption energy calculated in the manner described above with reference to FIG. 16 or 17. FIG. 18 shows an example of a calculation of the amount of fat burnt. It is known that when 1 kg of fat is burnt, about 7700 kcal of energy is consumed.

Thus, the amount of fat burnt can be determined by dividing the consumption energy (kcal) by 7700 kcal which is energy necessary to burn 1 kg of fat, and further multiplying the result by 1000 (g) to obtain a result consistent in terms of units.

In the example shown in FIG. 17 in which the user exercises in synchronization with music A to F registered in the music information list shown in FIG. 9, the consumption energy is calculated as 82.095 kcal as shown in (13) of FIG. 17, and thus the amount of fat burnt is calculated as 10.66 (g) as shown in (15) of FIG. 18.

As described above, the exercise time, the walking distance, the average speed, the consumption energy (in calories), and the amount of fat burnt can be calculated based on the personal profile information of the user who exercises while listening to music played by the audio playback apparatus 1 according to the present embodiment, and based on the attribute information of music played. The determination in step S113 can be made based on the exercise time and the consumption energy calculated in step S112 in FIG. 5 in the manner described above with reference to FIGS. 14 to 18. On the basis of the calculated cumulative total amount of exercise, the amount of exercise performed by the user is displayed in step S116 in the manner described above with reference to FIG. 12.

In the case where the target amount of exercise is set by specifying one or more exercise types and corresponding exercise times as in the manner described above with reference to FIG. 8, the exercise type (the running type) is automatically determined and the exercise time for each exercise type is determined in step S112 as described above.

The exercise time, for which the user has actually performed the exercise, is compared with the target exercise time (the planned exercise time) for each exercise type (each planned exercise type). If the target amount of exercise is satisfied for all exercise types, it is determined that the goal has been achieved.

In the case where the target amount of exercise is set by specifying one or more exercise types and corresponding exercise times as in the manner described above with reference to FIG. 8, the user does not necessarily perform exercise exactly according to the plan. For example, when it is planned to perform jogging for 30 minutes, the user may actually perform jogging for 15 minutes, walking for 5 minutes, and then jogging for 10 minutes. In step S113, the determination as to whether the target amount of exercise has been achieved may be made only based on the exercise time, and exercise execution history may be produced as shown in FIG. 13B.

MET Value

The MET value indicating the strength of exercise used in the calculation of consumption energy described above with reference to FIG. 17 is described in further detail below with reference to FIGS. 19 and 20. The MET value is given by dividing oxygen uptake during exercise by oxygen consumption in a resting state according to formula (16) in FIG. 19.

In FIG. 19, the oxygen consumption in the resting state is denoted by R, the horizontal moving component indicating the oxygen consumption due to horizontal movement is denoted by H, and the vertical moving component indicating the oxygen consumption due to vertical movement is denoted by V. The horizontal moving component in walking is given by 0.1× the speed according to formula (18) in FIG. 19, and the horizontal moving component in running is given by 0.2× the speed according to formula (19) in FIG. 19. The vertical moving component is given by 0.9×speed×tilt according to formula (20) in FIG. 19.

The oxygen uptake during exercise is given by (R+H+V) according to formula (17) in FIG. 19. The oxygen consumption in the resting state is given by R as described above, and thus the MET value is given by (R+H+V)/R according to formula (16) in FIG. 19. As shown in FIG. 19, 1 MET corresponds to oxygen consumption of 3.5 ml/kg·min which is equal to oxygen consumption in the resting state.

FIG. 20 shows two specific examples of calculations of the MET value. In a first example, the MET value is calculated for a case where walking is performed at a speed of 6 km/hour. As described above with reference to FIG. 19, the MET value can be determined from the oxygen consumption in the resting state R, the horizontal moving component H, and the vertical moving component V. Because the oxygen consumption at the resting state R is equal to 3.5 ml/kg·min as described above with reference to FIG. 19, the MET value can be calculated if the horizontal moving component H and the vertical moving component V are given.

The horizontal moving component H in walking is given by 0.1×speed 1/min according to formula (18) in FIG. 19. When walking is performed at a speed of 6 km/hour, the speed in units of km/hour can be converted into a value in units of m/min as 100 m/min. Thus, the horizontal moving component H can be calculated as 10.0 ml/kg·min according to formula (21) in FIG. 20. On the other hand, the vertical moving component V is given as 0.9×speed (m/min)×tilt according to formula (20) in FIG. 19. When walking is performed in a flat place, no tilt occurs during exercise. Thus, tilt=0 rad (%) in formula (22) in FIG. 20, and the vertical moving component V becomes 0.

The oxygen uptake during exercise is determined by adding the oxygen consumption in the resting state R, the horizontal moving component H, and the vertical moving component V according to formula (23) in FIG. 20. The MET value is then determined by dividing the oxygen uptake during exercise by the oxygen consumption in the resting state R according to formula (24) in FIG. 20. In this specific example, the MET value for walking at a speed of 6 km/hour is calculated as 3.9.

Next, by way of example, the MET value is calculated for a case where jogging is performed at a speed of 10 km/hour. Also in this case, the oxygen consumption in the resting state R is already known as in the case of walking, and thus the MET value can be calculated of the horizontal moving component H and the vertical moving component V are given. Using the value of the running speed converted from an expression in units of km/hour into an expression in units of m/min, 166.7 m/min, the horizontal moving component H is calculated as 33.34 ml/kg·min according to formula (25) in FIG. 20.

In running, in general, no tile occurs during exercise as in the case of walking. Thus, tilt=0 rad (%) in formula (26) in FIG. 20, and the vertical moving component V becomes 0.

The oxygen uptake during exercise is determined by adding the oxygen consumption in the resting state R, the horizontal moving component H, and the vertical moving component V according to formula (27) in FIG. 20. The MET value is then determined by dividing the oxygen uptake during exercise by the oxygen consumption in the resting state R according to formula (28) in FIG. 20. In this specific example, the MET value for running at a speed of 10 km/hour is calculated as 10.5.

The MET value indicating the strength of exercise can be determined in the above-described manner for each exercise type. Furthermore, using the MET value determined in the above-described manner, the consumption energy can be determined as weight×MET value×exercise time according to formula (11) in FIG. 17.

FIG. 21 shows an example of a calculation of the consumption energy (in calories) using a MET value for a case where a person with a weight of 60 kg runs across a flat place at a speed of 10 km/hour (166.7 m/min) for 30 minutes. First, the MET value is calculated as (3.5+166.7×0.2)/3.5 according to formula (29) in FIG. 21. The MET value is then multiplied by the weight (60 kg) and further by the time (30/60 hours). Thus, the consumption energy is determined as 315.77 kcal.

FIG. 22 shows a detailed expression of a formula for determining consumption energy based on a MET value. Consumption energy for walking is calculated as follows. First, a speed Vi of one step is calculated by dividing a step size Ww by an exercise time (time needed for one step) Ti according to formula (30) in FIG. 22.

From the speed Vi of one step, the horizontal moving component is determined as described above with reference to FIG. 19. When exercise is performed at a sloped place, the vertical moving component is determined from the slope. When walking is performed at a flat place, no tilt occurs. Thus, the MET value per step can be determined from the horizontal moving component according to formula (17) in FIG. 19.

The energy consumed by the exercise is given by the sum of products of the weight, the MET value (MET(Vi)) determined from the speed Vi of one step, and the exercise time Ti of one step taken over the total exercise time. The mathematical expression (31) in FIG. 22 can be rewritten into a simpler expression (32) in FIG. 22.

Typical MET values are as follows. The MET value for walking at a speed of 3.2 km/hour is 2 to 3. The MET value for walking at a speed of 4.8 km/hour is 3 to 4. The MET value for walking at a speed of 6.4 km/hour is 5 to 6. The MET value for walking at a speed of 8 km/hour is 6 to 7.

The MET value for jogging at a speed of 8 km/hour is 7 to 8. The MET value for jogging at a speed of 10 km/hour is 11. The MET value for jogging at a speed of 12 km/hour is 12.5. The MET value is also determined for other various exercise types. The MET value is rather high for cycling, aerobics dance, skipping rope, racquetball, etc.

As described above, if personal profile information indicating the weight, the height, and the step size of a user and attribute information indicating the tempo of music played during exercise are given, exercise information including the amount of exercise performed by the user can be easily, quickly, and accurately determined, and can be presented to the user. The result may be stored and analyzed. When the personal profile information includes further detailed information in terms of the age, the sex, etc. of the user, detailed exercise information can be calculated more accurately and can be used.

Moving Tempo and Determination of Exercise Type

In the present embodiment, the exercise information analysis circuit 23 of the audio playback apparatus calculates the moving tempo and determines the exercise type, as described below. FIG. 23 shows a vertical component signal output from the three-axis acceleration sensor used as the exercise information sensor 24. In FIG. 23, a horizontal axis represents time (sec) and a vertical axis represents a voltage (mV).

The exercise information analysis circuit 23 detects a repetition peak period of the signal such as that shown in FIG. 23 output from the exercise information sensor 24, and detects a moving tempo from the repetition peak period. More specifically, the autocorrelation of the detection signal output from the exercise information sensor 24 is calculated thereby removing noise components. Peak values are then detected, and the peak period is determined. Thus, the moving tempo can be accurately detected.

As can be seen from FIG. 23, the vertical component of the acceleration for jogging is 2 to 3 times greater than that for walking, and thus it is possible to determine from the vertical component of the acceleration whether a user is walking or jogging.

In many cases, a user performs walking or jogging while listening to music. However, this is not always the case. A user may perform cycling or skipping rope while listening to music. For such types of exercises, it is also possible to detect the exercise type by analyzing the detection signal output from the exercise information sensor 24.

When a user performs exercise of a type that is difficult to detect from the detection signal output from the exercise information sensor 24, the user may input or select an exercise type and exercise strength via the key operation unit so that the audio playback apparatus according to the present embodiment can operate based on the input exercise type and exercise strength.

Information Processing Apparatus and Service Information Providing Apparatus

Examples of the configuration of the information processing apparatus 2 and the service information providing apparatus 3 in the health exercise assist system, and their operations are described below. Before the description, information transmitted among apparatus including the audio playback apparatus 1 in the health exercise assist system according to the present embodiment is discussed briefly.

Figure 24:
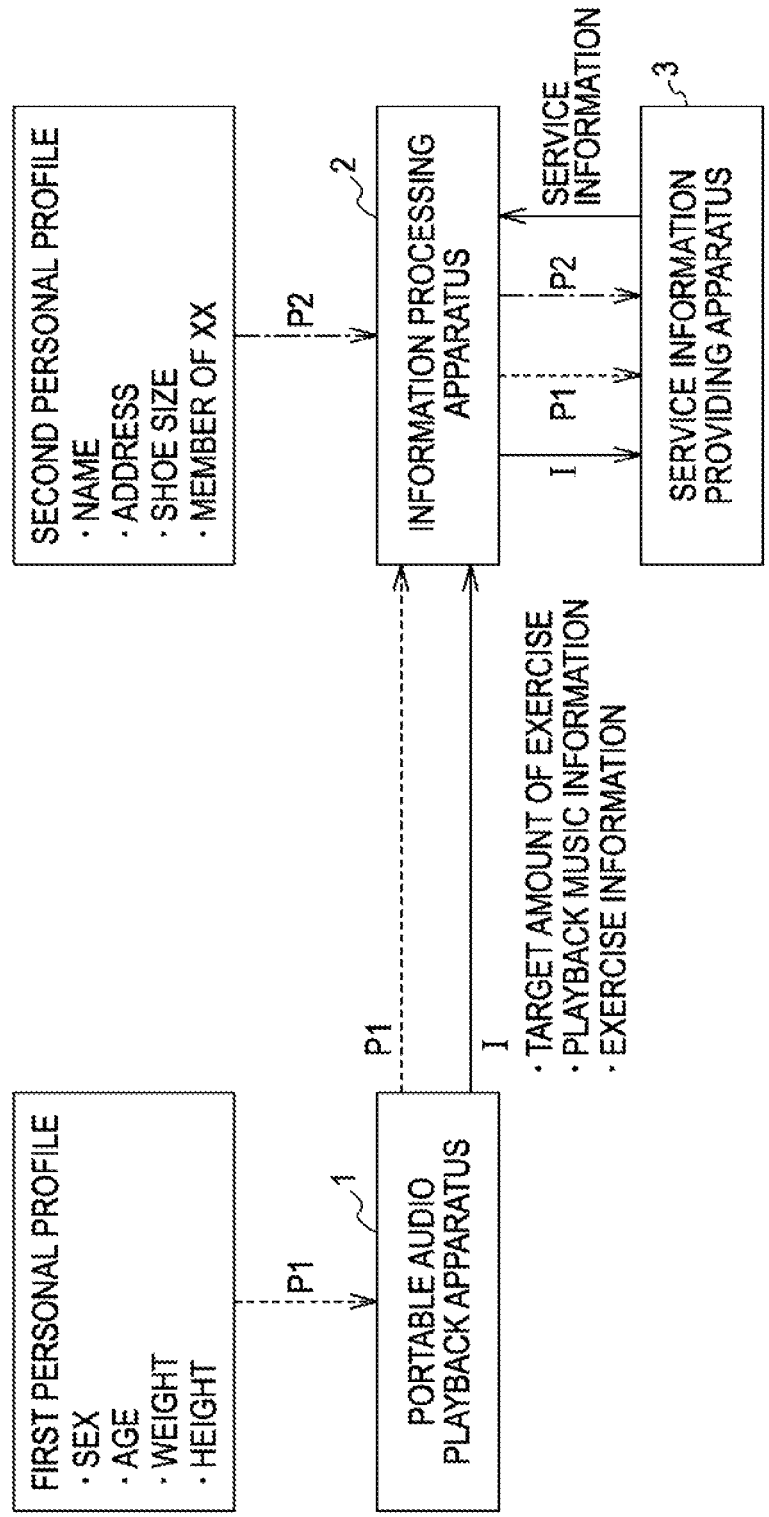
FIG. 24 is a diagram illustrating various kinds of information transmitted in a health exercise assist system including an audio playback apparatus, an information processing apparatus, and a service information providing apparatus.

FIG. 24 shows information transmitted among the audio playback apparatus 1, the information processing apparatus 2, and the service information providing apparatus 3 in the health exercise assist system according to the present embodiment. As described above with reference to FIGS. 4 and 6, personal profile information indicating the name, the sex, the age, the height, the weight, BMI, the degree of obesity of the user of the audio playback apparatus 1 is input to the audio playback apparatus 1. Note that it is not necessarily needed to input all those items of the personal profile information.

For example, as shown in FIG. 24, it is allowed to input only items such as the weight and the height, which can vary each time exercise is performed, to the audio playback apparatus 1 each time exercise is performed. In the present example, information of such items is denoted as first personal profile information P1. In addition to the weight and the height, the first personal profile information P1 may also include the sex and the age of the user so that the first personal profile information P1 can be identified by the age and the sex when the audio playback apparatus 1 is shared by particular limited persons such as family members.

Of items of personal profile information, items such as the name, the address, the shoe size, membership of an organization and the like of the user of the audio playback apparatus 1, which rarely change, are registered as second personal profile information in the information processing apparatus 2 installed at a home or the like, as shown in FIG. 24.

As described above, the target amount of exercise (exercise plan) is input to the audio playback apparatus 1. when the user performs exercise while listening to music played by the audio playback apparatus 1, the audio playback apparatus 1 acquires history information including playback music information and exercise information and stores the acquired history information.

The first personal profile information P1, and the acquired information I including the target amount of exercise and the history information (playback music information and exercise information) are transmitted from the audio playback apparatus 1 to the information processing apparatus 2 installed at the home of the user.

The information processing apparatus 2 produces a service request including the first personal profile information P1 and the acquired information I including the target amount of exercise and the history information supplied from the audio playback apparatus 1, and also including the second personal profile information P2 stored in the information processing apparatus 2, and the information processing apparatus 2 sends the service request to a particular service information providing apparatus 3 on a network such as the Internet.

If the service information providing apparatus 3 receives from the information processing apparatus 2 the service request including the acquired information I including the target amount of exercise and the history information (playback music information and exercise information), the first personal profile information P1, and the second personal profile information P2, the service information providing apparatus 3 determines service information to be provided to the information processing apparatus 2, on the basis of information included in the received service request.

The service information providing apparatus 3 prepares information to be provided as the service information by producing the service information or by extracting information to be provided as the service information from information prepared in the service information providing apparatus 3, and the service information providing apparatus 3 returns the service information to the information processing apparatus 2 which is a sender of the service request.

Thus, the user of the audio playback apparatus 1 can use the service information provided by the service information providing apparatus 3 via the information processing apparatus 2. An example of service information is music data provided as a reward to the user depending on the level of the amount of exercise achieved by the user.

Information Processing Apparatus

An example of a configuration of the information processing apparatus 2 in the health exercise assist system according to the present embodiment and a basic operation thereof are described below with reference to FIGS. 25 and 26.

Figure 25:
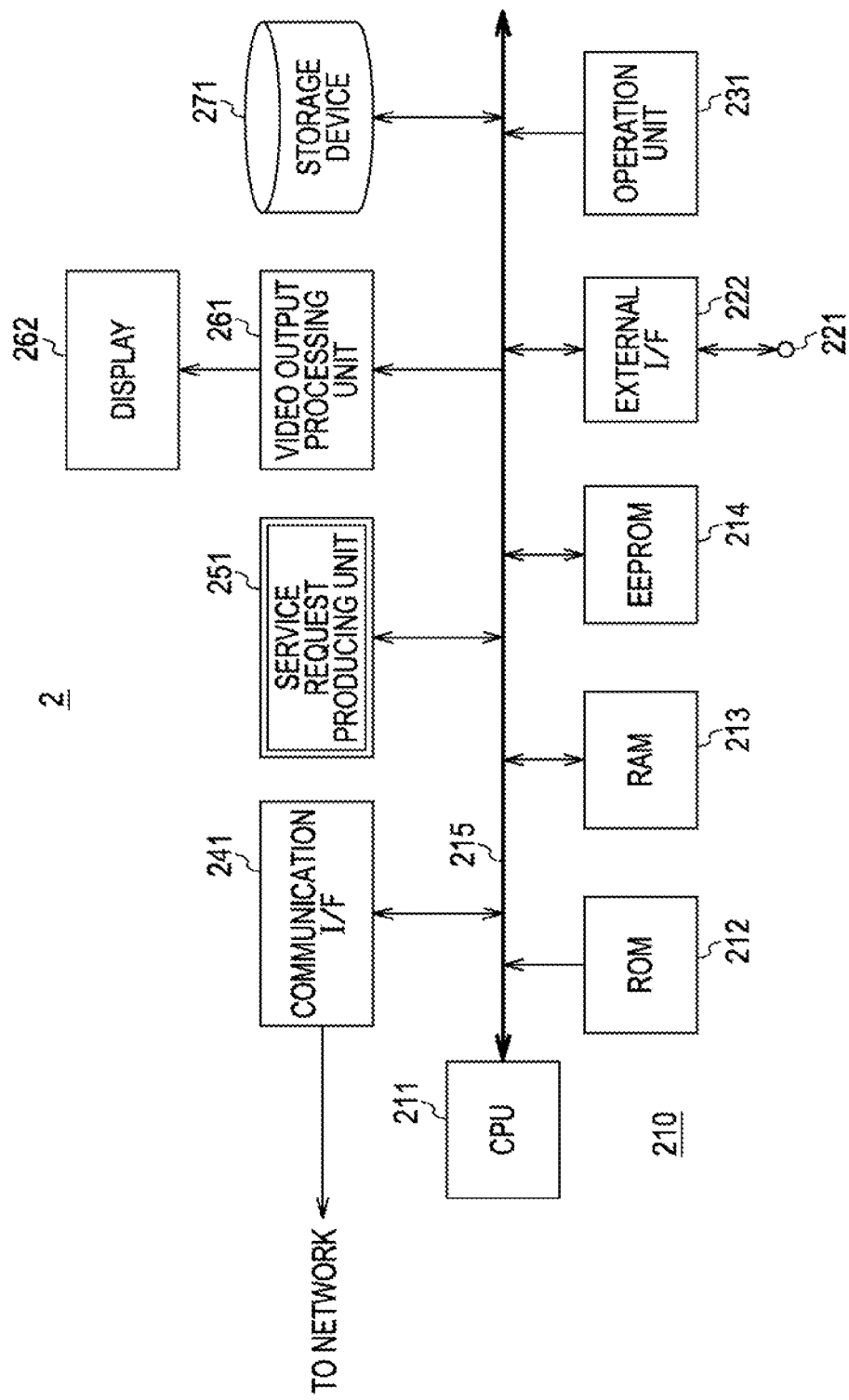
FIG. 25 is a block diagram illustrating an example of a configuration of an information processing apparatus.

FIG. 25 is a block diagram illustrating an example of a configuration of the information processing apparatus 2. As shown in FIG. 25, the information processing apparatus 2 according to the present embodiment includes a microcomputer serving as a control unit 210 including a CPU 211, a ROM 212, a RAM 213, and an EEPROM 214, which are connected to each other via a CPU bus 215.

The control unit 210 controls various parts of the information processing apparatus 2 according to the present embodiment. The CPU 211 is a main part responsible for the control operation, and is adapted to execute a program and supply control signals generated in the execution of the program to various parts of the information processing apparatus 2 thereby controlling the various parts. The ROM 212 stores various programs executed by the CPU 211 and various data used in the execution of programs. The RAM 213 is mainly used as a wok area for temporarily storing intermediate results of the like.

The EEPROM 214 is a nonvolatile memory used to retain information even after the power of the information processing apparatus 2 is turned off. The information stored in the EEPROM 214 includes, for example, various kinds of setting information, parameters, second personal profile information, etc.

As shown in FIG. 25, the control unit 210 is connected to an input/output terminal 221 via an external apparatus interface (I/F) 222, an operation unit 231, a communication interface (I/F) 241, and a service request producing unit 251. The control unit 210 is also connected to a display 262 via a video output processing unit 261, and to a storage device 271.

The input/output terminal 221 and the external apparatus interface 222 are for connecting to an external apparatus. For example, the audio playback apparatus 1 is connected to the information processing apparatus 2 via the input/output terminal 221 and the external apparatus interface 222. The operation unit 231 includes, for example, alphabetic keys, numeric keys, and various function keys whereby a user is allowed to input a command or information. If a command or information is input, a corresponding electric signal is supplied from the operation unit 231 to the control unit 210. In accordance with the command or information input via the operation unit 231, the control unit 210 controls various parts to perform a process to satisfy a request issued by the user.

The communication interface 241 is connected to a wide-area network such as the Internet, for transmission/reception of various kinds of data. The service request producing unit 251 produces a service request including the acquired information I and the first personal profile information P1 supplied from the audio playback apparatus 1 connected to the service request producing unit 251 via the input/output terminal 221 and the external apparatus interface 222, and also including second personal profile information stored in the EEPROM 214 of the service request producing unit 251.

The service request produced by the service request producing unit 251 is transmitted to the particular service information providing apparatus 3 via the communication interface 241 under the control of the control unit 210. In this transmission process, the particular service information providing apparatus 3 is identified, for example, by an IP address stored in the EEPROM 214. The functions of the service request producing unit 251 denoted by a double-line block in FIG. 25 may be implemented by a program executed by the CPU 211 in the control unit 210. That is, the control unit 210 may implement the functions of the service request producing unit 251.

The video output processing unit 261 produces, under the control of the control unit 210, an image signal (video signal) for displaying an image on the display screen of the display 262, in accordance with image information supplied from the control unit 210. The display 262 is implemented by a display device such as an LCD (Liquid Crystal Display), an EL (Electro Luminescence) panel, or a CRT (Cathode-Ray Tube) having a relatively large display screen on which to display various kinds of information.

On the display screen of the display 262, various kinds of information is displayed in accordance with the video signal produced by the video output processing unit 261 under the control of the control unit 10. For example, information input by a user via the operation unit 231, text information such as operation guidance, an error message, etc., and image information are displayed.

The storage device 271 is a storage medium drive on which a particular type of storage medium is mounted or installed. For example, when a recordable optical disk such as a CD (Compact Disc) or DVD (Digital Versatile Disc) is used as the storage medium, an optical disk drive is used as the storage device 271. When a hard disk is used as the storage medium, a hard disk drive is used as the storage device 271. When a semiconductor memory is used as the storage medium, a semiconductor memory drive is used as the storage device 271. In this specific example, a hard disk drive is used as the storage device 271.

Although not shown in FIG. 25, the information processing apparatus 2 according to the present embodiment may also include a speaker and an audio output processing unit for producing an audio signal to be supplied to the speaker, thereby allowing the information processing apparatus 2 to play music data. This makes it possible for the information processing apparatus 2 to operate such that music data is acquired from an external apparatus via the input/output terminal 221 and the external apparatus interface 222 or from a music server via the communication interface 241 and stored in the storage device 271 so that music data is read from the storage device 271 and played, or music data received in the form of stream data is directly played.

As described above with reference to FIG. 24, the control unit 210 of the information processing apparatus 2 configured as shown in FIG. 25 produces, by controlling the service request producing unit 251, a service request including the first personal profile information P1 supplied from the audio playback apparatus 1, the acquired information I including the target amount of exercise and the history information including the playback music information and the exercise information, and the second personal profile information P2 stored in the information processing apparatus 2, the control unit 210 transmits the produced service request to the particular service information providing apparatus 3 via the communication interface 241. If the information processing apparatus 2 receives, via the communication interface 241, service information transmitted from the service information providing apparatus 3 in response to the service request, the information processing apparatus 2 uses the received service information.

Now, a basic operation of the information processing apparatus 2 configured as shown in FIG. 25 is described below. FIG. 26 is a flow chart illustrating a process performed by the information processing apparatus 2 according to the present embodiment to transmit a service request, receive service information returned in response to the service request, and use the received service information.

Figure 26:
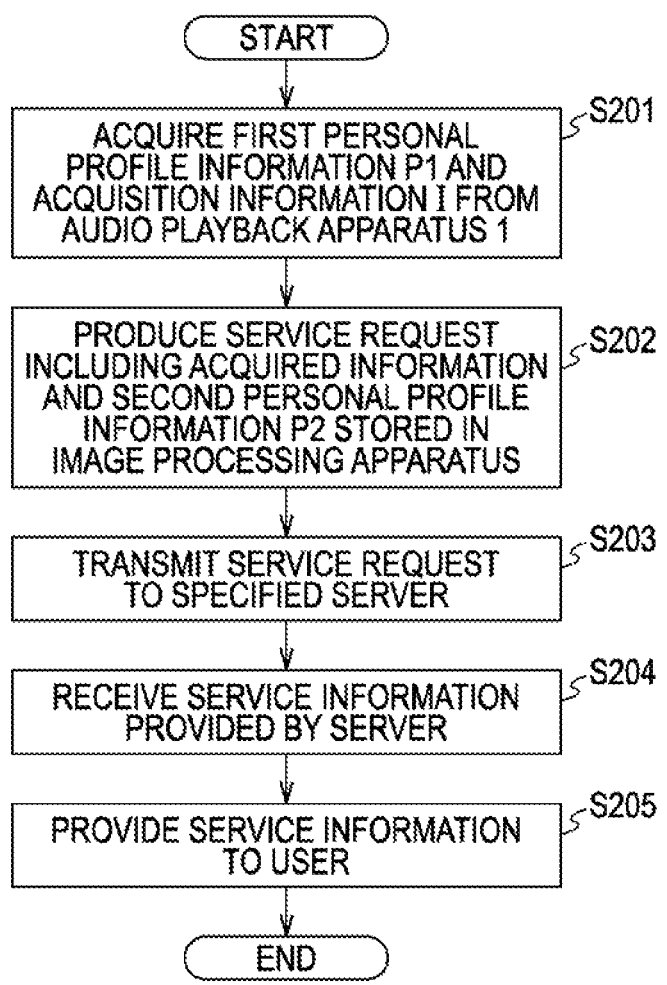
FIG. 26 is a flow chart illustrating a process performed by an information processing apparatus to receive service information and use the received service information.

In a state in which the audio playback apparatus 1 is connected to the input/output terminal 221 of the information processing apparatus 2, if a command to receive service information from the service information providing apparatus 3 is input via the operation unit 231, the control unit 210 starts the process shown in the flow chart of FIG. 26.

First, the control unit 210 receives, via the external apparatus interface 222, first personal profile information and acquired information I including a target amount of exercise and history information including playback music information and exercise information from the audio playback apparatus 1 connected to the input/output terminal 221 (step S201). The control unit 210 supplies, to the service request producing unit 251, the first personal profile information P1 and the acquired information I received from the audio playback apparatus 1 and the second profile information P2 stored in the memory of the information processing apparatus 2, and the control unit 210 controls the service request producing unit 251 to produce a service request including the above information (step S202).

The control unit 210 then controls the service request producing unit 251 and the communication interface 241 such that the service request produced by the service request producing unit 251 is supplied from the service request producing unit 251 to the communication interface 241, and is sent from the communication interface 241 to the particular service information providing apparatus 3 (step S203).

If the service information providing apparatus 3 receives the service request, the service information providing apparatus 3 acquires service information in accordance with the service request and returns the service information to the information processing apparatus 2 which is the requester of the service information. The information processing apparatus 2 receives this service information via the communication interface 241 (step S204).

The information processing apparatus 2 provides the received service information to the user so that the user can use it (step S205). Thus, the process shown in FIG. 26 is completed. More specifically, in step S205, the control unit 210 stores the received service information in the storage medium of the storage device 271 so that the user can read the service information from the storage medium and use it whenever the user wants to do so. When the service information is image information, the control unit 210 displays the image information given as the service information on the display 262 via the video output processing unit 261.

As described above, the information processing apparatus 2 is capable of producing a service request including information received from the audio playback apparatus 1 and information stored in the information processing apparatus 2, transmitting the produced service request to the particular service information providing apparatus 3, receiving service information transmitted from the service information providing apparatus 3 in response to the service request, and providing the received service information to the user.

Service Information Providing Apparatus

An example of a configuration of the service information providing apparatus 3 in the health exercise assist system according to the present embodiment and a basic operation thereof are described below with reference to FIGS. 27 and 28.

Figure 27:
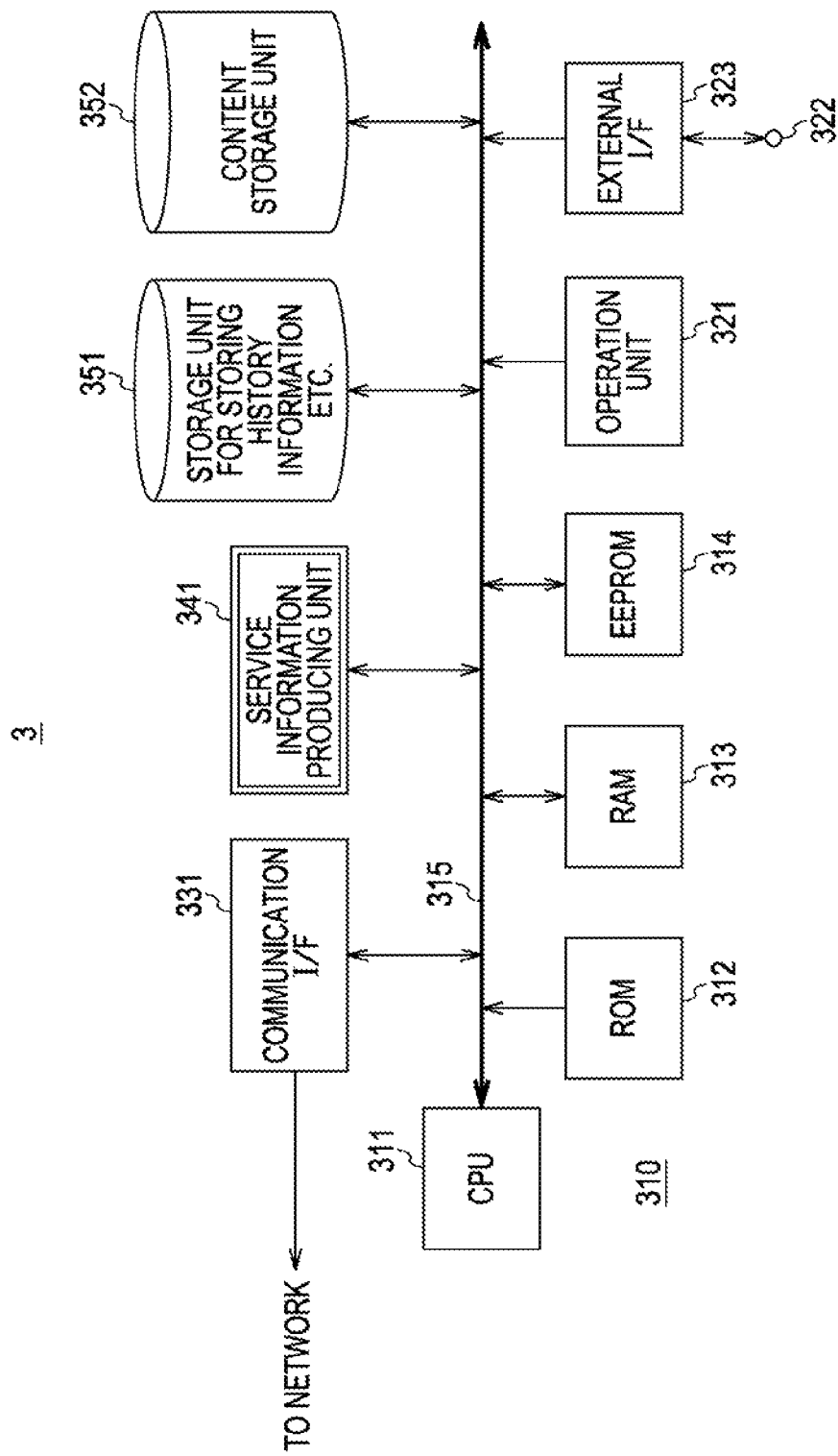
FIG. 27 is a block diagram illustrating an example of a configuration of a service information providing apparatus.

FIG. 27 is a block diagram illustrating an example of a configuration of the service information providing apparatus 3. As shown in FIG. 27, the service information providing apparatus 3 according to the present embodiment includes a microcomputer serving as a control unit 310 including a CPU 311, a ROM 312, a RAM 313, and an EEPROM 314, which are connected to each other via a CPU bus 315.

The control unit 310 controls various parts of the service information providing apparatus 3 according to the present embodiment. The CPU 311 is a main part responsible for the control operation, and is adapted to execute a program and supply control signals generated in the execution of the program to various parts of the service information providing apparatus 3 thereby controlling the various parts. The ROM 312 stores various programs executed by the CPU 311 and various data used in the execution of programs. The RAM 313 is mainly used as a wok area for temporarily storing intermediate results of the like. The EEPROM 314 is a nonvolatile memory used to retain information even after the power of the information processing apparatus 2 is turned off. The information stored in the EEPROM 314 includes, for example, newly added programs, various kinds of data, various kinds of setting information or parameters, etc.

As shown in FIG. 27, the control unit 310 is connected to an operation unit 321, an input/output terminal 322 via an external apparatus interface 323, a communication interface 331, a service information producing unit 341. a history information storage unit 351, and a content storage unit 352.

The operation unit 321 includes, for example, alphabetic keys, numeric keys, and various function keys whereby a user is allowed to input a command or information. If a command or information is input, a corresponding electric signal is supplied from the operation unit 321 to the control unit 310. In accordance with the command or information input via the operation unit 321, the control unit 310 controls various parts to perform a process to satisfy a request issued by the user. The input/output terminal 322 and the external apparatus interface 323 are for connecting to an external apparatus. That is, the input/output terminal 322 and the external apparatus interface 323 allow the service information providing apparatus 3 to be connected to an external apparatus.

The communication interface 331 is connected to a wide-area network such as the Internet, for transmission/reception of various kinds of data. The above-described service request transmitted from the information processing apparatus 2 is received via the communication interface 331 and supplied to the control unit 310. Under the control of the control unit 310, the service information producing unit 341 produces service information in accordance with the service request received via the communication interface 331 and the history information stored in the history information storage unit 351 described below, or the service information producing unit 341 extracts content information to be sent as the service information from content information stored in the content storage unit 352.

The history information storage unit 351 stores information included in the received service request separately for each user of the audio playback apparatus 1. The history information storage unit 351 makes it possible to calculate the cumulative amount of exercise separately for each of the audio playback apparatus 1. The content storage unit 352 stores various kinds of content information such as music data, image information, etc. together with information indicating provision conditions.

In the service information providing apparatus 3 according to the present embodiment, if a service request is received from the information processing apparatus 2 via the communication interface 331, the control unit 310 reads history information associated with the user who issued the service request from the history information storage unit 351 in accordance with the second personal profile information included in the service request, and the control unit 310 supplies the service request and the history information to the service information producing unit 341 to produce the service information to be returned.

The service information producing unit 341 produces service information on the basis of the service request supplied via the control unit 310 and the history information read from the history information storage unit 351 or produces service information by extracting content information from the content storage unit 352.

The service information producing unit 341 calculates the cumulative amount of exercise performed by the user on the basis of the exercise information included in the service request and the exercise information described in the history information supplied from the history information storage unit 351, and the service information producing unit 341 produces service information depending on the calculated cumulative amount of exercise. For example, message information is produced as the service information depending on the cumulative amount of exercise, or music data or image data to be rewarded as the service information is extracted from the content storage unit 352, depending on the cumulative amount of exercise.

The control unit 310 analyzes information included in the service request to identify the information processing apparatus 2 which is the sender of the service request, and transmits service information produced by the service information producing unit 341 in the above-described manner over a network via the communication I/F 331 thereby providing the service information to the information processing apparatus 2 which is the sender of the service request.

Now, a basic operation of the service information providing apparatus 3 configured as shown in FIG. 27 is described below. FIG. 28 is flow chart illustrating a process performed by the service information providing apparatus 3 according to the present embodiment to produce service information in accordance with the service request received from the information processing apparatus 2 and return the produced service information to the information processing apparatus 2.

Figure 28:
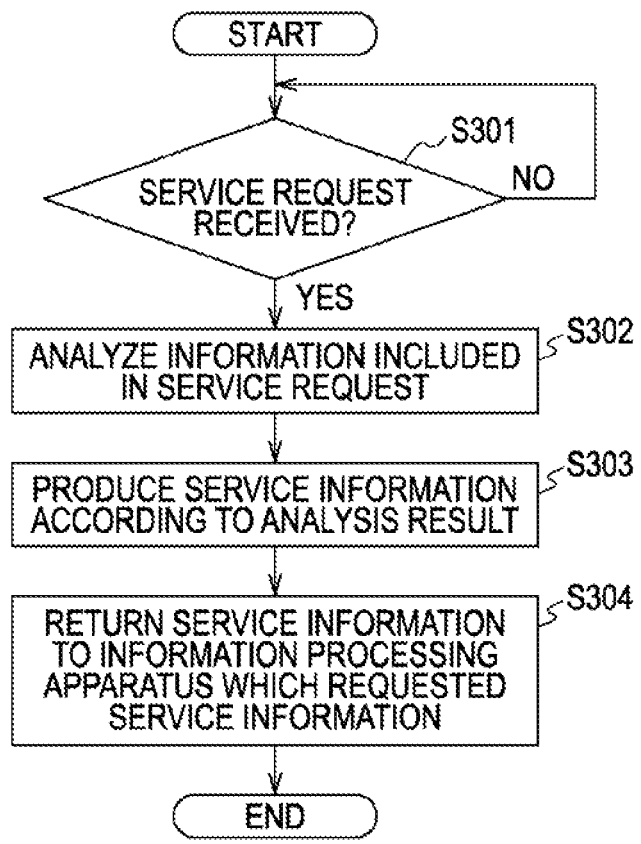
FIG. 28 is a flow chart illustrating a process performed by a service information providing apparatus to produce service information and return the produced service information.

In the service information providing apparatus 3 configured to respond to a service request, the control unit 310 performs the process shown in FIG. 28. The control unit 310 monitors information transmitted from the communication interface 331 until a service request addressed to the service information providing apparatus 3 is detected (step S301). If it is determined in step S301 that a service request addressed to the service information providing apparatus 3 is received, the control unit 310 control the service information producing unit 341 to analyze information included in the received service request, i.e., the target amount of exercise, the history information in terms of played music and performed exercise (step S302).

Note that, as described above, the process in step S302 includes determining the cumulative amount of exercise, the cumulative exercise time, and other necessary information taking into account the history information for a particular user of interest stored in the history information storage unit 351.

The control unit 310 then controls the service information producing unit 341 to produce service information to be provided to the information processing apparatus 2 which is the requester of the service information, in accordance with the result of the analysis performed in step S302 (step S303). In this step S303, more specifically, information to be provided to the information processing apparatus 2 is produced depending on the amount of exercise performed, or music data or image data to be rewarded is extracted from the content storage unit 352, depending on the amount of exercise.

The control unit 310 transmits the service information produced by the service information producing unit 341 in step S303 to the information processing apparatus 2 which is the requester of the service information via the communication interface 331 (step S304). Thus, the process shown in FIG. 28 is completed.

As described above, the service information providing apparatus 3 is adapted to produce service information in response to a service request received from the information processing apparatus 2, and transmit the produced service information to the information processing apparatus 2 which is the requester of the service information, so that the user of the audio playback apparatus 1 can use the service information via the information processing apparatus 2.

Specific Examples of Service Information

Specific examples of services provided by the service information providing apparatus 3 in the health exercise assist system according to the present embodiment are described below with reference to FIGS. 29 to 31.

Music Content Service

Figure 29A:
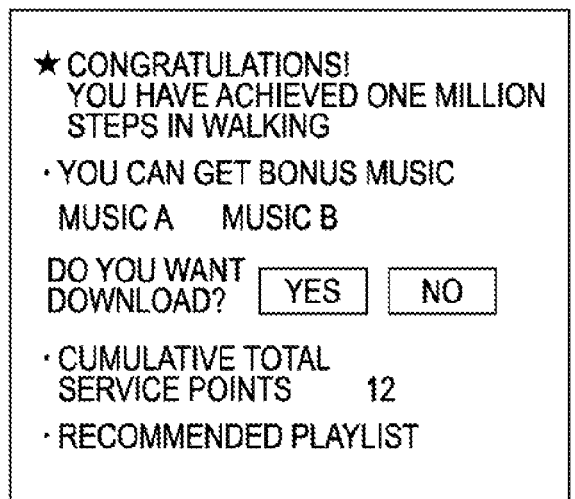
FIGS. 29A and 29B illustrate specific examples of services provided by service information providing apparatus.

FIG. 29A illustrates an example of service information provided by the service information providing apparatus 3 for a case where the service information providing apparatus 3 is the music server 3-1 shown in FIG. 1. The music server 3-1 is adapted to, in response to a request from a user, provide music data (music content) at no or some fee via the network 100.

A special service provided by the music server 3-1 according to the present embodiment is to provide a free music content as a reward when the user of the audio playback apparatus 1 has performed 100,000 steps or more of walking, jogging, or running while listening to music played by the audio playback apparatus 1 worn on the user.

More specifically, as described above, the audio playback apparatus 1 according to the present embodiment produces an exercise execution history including information played music and performed exercise and stores the exercise execution history in the storage device 53 of the audio playback apparatus 1, each time the user performs exercise such as walking, jogging, or running in synchronization with music played by the audio playback apparatus 1 worn on the user.

At a proper time after exercise is performed, if the user connects the audio playback apparatus 1 to the information processing apparatus 2 installed at the home of the user and performs a particular operation on the audio playback apparatus 1, the control unit 210 of the information processing apparatus 2 acquires the exercise execution history such as that shown in FIG. 13B and the first personal profile information from the audio playback apparatus 1 and produces a service request including the acquired information and second personal profile information stored in the information processing apparatus 2. The control unit 210 of the information processing apparatus 2 transmits the produced service request to the music server 3-1 via the communication interface 241.

The control unit 310 of the music server 3-1, which is one of service information providing apparatuses 3, receives the service request from the information processing apparatus 2 via the communication interface 331 and manages the cumulative number of steps described in the exercise information in the exercise execution history included in the service request, separately for each user. More specifically, the music server 3-1 manages the cumulative number of steps for each user by using, as key information, identification information uniquely identifying each user of the audio playback apparatus 1, such as a name of each user, included in the service request.

Each time a service request is received, the control unit 310 of the music server 3-1 calculates the cumulative number of steps for each user. If a user is detected who has reached 100,000 steps in cumulative number, the control unit 310 produces display information including a message indicating that the cumulative number of steps has reached 100,000 steps, a message indicating that the user is allowed to download free music contents, "MUSIC A" and "MUSIC B", as a reward for the achievement of 100,000 steps, a "YES" icon used to issue a command to download bonus music contents, a "NO" icon used to issue a command not to download bonus music contents, a numeric value indicating the cumulative number of service points, and a message indicating that a recommended playlist is available, and the control unit 310 transmits the produced display information as first-provided service information to the information processing apparatus 2 which is the requester of the service via the communication interface 331.

If the information processing apparatus 2 receives the display information from the music server 3-1 which is one of the service information providing apparatuses via the communication interface 241, the control unit 210 supplies the received display information to the display 262 via the video output processing unit 261 to display the display information shown in FIG. 29A on the display screen 262G of the display 262. The information processing apparatus 2 then receives a command input by the user via the operation unit 231.

When the user decided to download bonus music data (downloadable for free), the user selects "MUSIC A" or "MUSIC B" and presses the "YES" icon. In response, the control unit 210 of the information processing apparatus 2 produces a request for the selected bonus music data and transmits it to the music server 3-1 via the communication interface 241.

If the control unit 310 of the music server 3-1 receives the request for the bonus music from the information processing apparatus 2 via the communication interface 331, the control unit 310 extracts the requested music data from the content storage unit 352 and transmits it to the information processing apparatus 2 which is the requester via the communication interface 331.

If the information processing apparatus 2 receives the bonus music data via the communication interface 241, the control unit 210 stores the received music data in the storage medium of the storage device 271 so that the music data can be played by the information processing apparatus 2 or the music data is transferred to the audio playback apparatus 1 via the external apparatus interface 222 and the input/output terminal 221 so that the music data can be played by the audio playback apparatus 1.

When the user decided not to download bonus music data because the user already has the same music data or the user is not interested in it, the user presses the "NO" icon to notify the control unit 210 of the information processing apparatus 2 that the user has decided not to download bonus music data. In response, the control unit 210 of the information processing apparatus 2 produces information indicating that it has been decided not to download the bonus music data, and the control unit 210 transmits it to the music server 3-1 via the communication interface 241 to notify that downloading of the bonus music data is not requested. In this case, another music data may be provided as bonus music data, or, instead of providing bonus music data, a service point may be presented.

The cumulative service point is the sum of points given depending on the number of music data purchased by the user or depending on the purchase price. Various kinds of services are provided to the user depending on the point. For example, one point corresponds to 100 yen, and points are used to purchase music data or other items such as a handkerchief, a T-shirt, a doll, a gift certificate, a travel coupon, etc. depending on the cumulative service point.

When information indicating the cumulative service point is provided to the user, the user may do nothing or may issue a command to use the cumulative service point. If the command to use the cumulative service point is issued, the control unit 210 of the information processing apparatus 2 produces a service request depending on the cumulative service point and transmits it to the music server 3-1 via the communication interface 241.

If the control unit 310 of the music server 3-1 receives the service request using the cumulative service point via the communication interface 331, the control unit 310 produces a list of services available depending on the cumulative service point of the user of the information processing apparatus 2, and transmits the list to the information processing apparatus 2 which is the sender of the service request via the communication interface 331.

If the control unit 210 of the information processing apparatus 2 receives the list of available services depending on the cumulative point via the communication interface 241, the control unit 210 supplies the list to the display 262 via the video output processing unit 261 to display the list on the display screen of the display 262 so that the user is allowed to request to provide a service such as music data or a gift selected from the list.

The recommended playlist is a list of music data recommended by the music server 3-1. The recommended playlist is produced by the music server 3-1 on the basis of a preference of the user for music detected by analyzing the playback music information included in service requests received in the past or by analyzing the history of downloading of music data performed by the user of the information processing apparatus 2 which is the issuer of the service request.

If the user selects to use the recommended playlist, the control unit 210 of the information processing apparatus 2 produces a request for the recommended playlist and transmits the request to the music server 3-1 via the communication interface 241.

If the control unit 310 of the music server 3-1 receives the request for the recommended playlist via the communication interface 331, the control unit 310 of the music server 3-1 detects the preference of the user of the information processing apparatus 2 in terms of music by analyzing the history of playback of music or a purchase history, and produces a recommended playlist including a plurality of pieces of music data which satisfies the preference of the user and which have not yet downloaded. The produced playlist of recommended music is transmitted to the information processing apparatus 2 which is the issuer of the request to the communication interface 331.

If the control unit 210 of the information processing apparatus 2 which is the issuer of the request receives the recommended playlist via the communication interface 241, the control unit 210 transfers the recommended playlist to the display 262 via the video output processing unit 261 to display the recommended playlist on the display screen of the display 262 so that the user is allowed to request to provide music data selected from the recommended playlist. The recommended playlist may include various kinds of music information in addition to a simple list of music data.

Virtual Travel Service

Figure 29B:
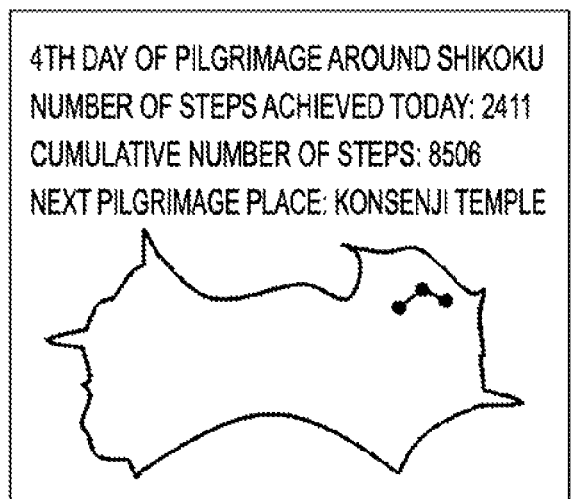

FIG. 29B illustrates service information provided by the service information providing apparatus 3 when the service information providing apparatus 3 is the exercise assist server 3-2 shown in FIG. 1. The exercise assist server 3-2 assists the user of audio playback apparatus 1 to perform everyday exercise such as walking, jogging, or running for a long period.

In the present example, the exercise assist server 3-2 is adapted to allow the user of the audio playback apparatus 1 to have a virtual experience of a travel along a predetermined route such that the virtual travel proceeds as the cumulative walking distance increases in the exercise such as walking, jogging, or running performed by the user of the audio playback apparatus 1 while listening to music played by the audio playback apparatus 1 worn on the user. In the specific example shown in FIG. 29B, a virtual pilgrimage travel across 88 holy places in Shikoku Island is provided.

In this example, as in the music content service described above, each time the user of the audio playback apparatus 1 performs exercise such as walking, jogging, or running in synchronization with music played by the audio playback apparatus 1, the exercise execution history including information indicating music played and information indicating exercise performed, such as that shown in FIG. 13B, is stored in the storage device 53 of the audio playback apparatus 1.

If the user connects the audio playback apparatus 1 to the information processing apparatus 2 installed at the home of the user and performs a particular operation on the audio playback apparatus 1, the control unit 210 of the information processing apparatus 2 acquires the exercise execution history such as that shown in FIG. 13B and the first personal profile information from the audio playback apparatus 1 and produces a service request including the acquired information and second personal profile information stored in the information processing apparatus 2. The control unit 210 of the information processing apparatus 2 transmits the produced service request to the exercise assist server 3-2 via the communication interface 241.

The control unit 310 of the exercise assist server 3-2, which is one of service information providing apparatuses 3, receives the service request from the information processing apparatus 2 via the communication interface 331 and manages the cumulative number of steps described in the exercise information in the exercise execution history included in the service request, separately for each user. More specifically, the exercise assist server 3-2 manages the cumulative number of steps for each user by using, as key information, identification information uniquely identifying each user of the audio playback apparatus 1, such as a name of each user, included in the service request. In the present embodiment, the exercise assist server 3-2 acquires in advance information indicating the distance between each two adjacent holy places for all 88 holy places on the pilgrimage route.

Each time the control unit 310 of the exercise assist server 3-2 receives a service request, the control unit 310 detects the cumulative walking distance separately for each user, and the control unit 310 calculates a virtual distance walked along the pilgrimage route in Shikoku island on the basis of the correspondence between the actually walked distance and the distance along the pilgrimage route. Information necessary to display a trace virtually achieved along the pilgrimage route corresponding to the calculated virtual distance walked on a map and other information to be displayed is transmitted from the control unit 310 to the information processing apparatus 2 which is the issuer of the request via the communication interface 331.

More specifically, display information including the count value of days in which the pilgrimage along holy places in Shikoku island was virtually performed as the exercise was actually performed (the count value equals to the total number of days in which the exercise was actually performed), the number of steps walked today, the cumulative number of steps walked, a holy place to visit next (a next destination), and the virtual trace walked along the pilgrimage route, which are to be displayed, as shown in FIG. 29B, on the display screen 262G of the display 262 of the information processing apparatus 2, is produced and transmitted to the information processing apparatus 2 which is the issuer of the request via the communication interface 331.

The total number of days in which the exercise was performed is calculated from the date information which is included in the exercise execution history stored in the storage device 53 of the audio playback apparatus 1 and which is transmitted together with the service request from the information processing apparatus 2 to the exercise assist server 3-2. Each time the exercise assist server 3-2 detects a change in date described in the exercise execution history included in the service request, the exercise assist server 3-2 increments the count of days in which the exercise was performed. The count of days is regarded as the number of days in which the pilgrimage in Shikoku Island was performed and displayed.

The number of steps walked today is acquired directly from the information indicating the number of steps described in the exercise execution history included in the latest received service request. The cumulative number of steps walked is given by the total number of steps walked during a period from the first day on which the exercise was started to the current day. The exercise assist server 3-2 determines the moving distance (the walking distance) by multiplying the step size determined from the running type described in the exercise execution history included in the received service request and the height of the user by the number of steps, and determines the cumulative moving distance by summing the individual moving distances.

The cumulative distance along the virtual pilgrimage route corresponding to the actual cumulative moving distance is calculated, and a next destination in the virtual pilgrimage is correctly determined. Information indicating the determined next destination is included into the display information to be displayed. Furthermore, information necessary to display the trace already walked along the virtual pilgrimage route on the map of Shikoku Island as shown in FIG. 29B is also included into the display information.

The display information necessary to display various kinds of information as shown in FIG. 29B is produced by the control unit 310 of the exercise assist server 3-2 in the above-described manner, and transmitted to the information processing apparatus 2, which issued the service request, via the communication interface 331.

If the control unit 210 of the information processing apparatus 2 receives the service information (the display information) from the exercise assist server 3-2 via the communication interface 241, the control unit 210 transfers the received service information to the display 262 via the video output processing unit 261 to display the service information on the display screen 262G of the display 262 as shown in FIG. 29B.

Thus, each time the user of the audio playback apparatus 1 performs everyday exercise such as walking, jogging, or running in a nearby place such as a park, the moving distance virtually walked along the pilgrimage route and a holy place to visit next are displayed. This motivates the user to continue the monotonous exercise such as walking, jogging, or running.

Each time the user reaches or passes a holy place, a photographic image of the holy place and/or information about the holy place such as a history thereof may be provided so that the user is allowed to make a virtual visit via the information processing terminal 2. Service points may be given to the user depending on the walking distance, and a right to apply for a gift may be given depending on the acquired points. Alternatively, a gift may be given without needing application, depending on the acquired points.

In this specific example, the virtual pilgrimage route in Shikoku Island is provided as the virtual travel route. The virtual travel route is not limited to the pilgrimage route in Shikoku island, but a wide variedly of virtual travel courses may be provided, such as an Okuno-Hosomichi course in which a user virtually travels along the same route as the route called "Okuno-Hosomichi" along which a great poet Basho Matsuo traveled, a virtual travel course across Japanese Islands, a virtual world travel course, a virtual travel along the Paris-Dakar rally course, and a virtual travel along the Silk Road.

Each user of the audio playback apparatus 1 is allowed to select a desired virtual travel course depending on a target amount of exercise and/or a planned period during which the exercise will be performed. Depending on the selected virtual course, the user is assisted to perform the exercise.

In the example described above, a virtual travel proceeds along a predetermined virtual route by a distance corresponding to an amount of exercise performed in a nearby place such as a park, and thus the user can easily enjoy the virtual travel. Alternatively, a user may actually travel along a particular course. In this case, each time the user arrives at an intermediate destination, the user may input information identifying the intermediate destination or a date when the user arrived at the intermediate destination so that the amount of exercise can be calculated from the input information.

Health Exercise Management Service

Figure 30A:
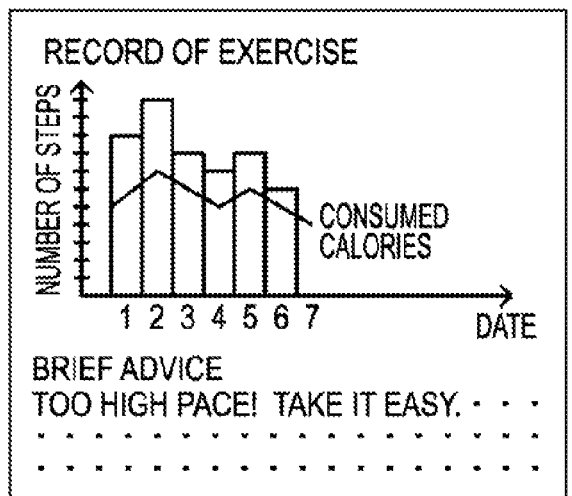
FIGS. 30A and 30B illustrate specific examples of services provided by service information providing apparatus.

FIG. 30A illustrates service information provided by the health assist server 3-3 shown in FIG. 1 selected as the service information providing apparatus 3. The health assist server 3-3 assists a user to perform exercise in a proper manner. More specifically, when the user of the audio playback apparatus 1 performs everyday exercise such as walking, jogging, or running or other types of exercise, the health assist server 3-3 assists the user to perform exercise by an optimal amount, a significant upward deviation from which will lead to ruining health of the user, but a significant downward deviation will give no effect of the exercise to the user.

Also in this case, as with music content service, when the user of the audio playback apparatus 1 performs exercise such as walking, jogging, or running in synchronization with music played by the audio playback apparatus 1 worn on the user, an exercise execution history including information played music and performed exercise and is produced and stored in the storage device 53 of the audio playback apparatus 1.

If the user connects the audio playback apparatus 1 to the information processing apparatus 2 installed at the home of the user and performs a particular operation on the audio playback apparatus 1, the control unit 210 of the information processing apparatus 2 acquires the exercise execution history such as that shown in FIG. 13B and the first personal profile information from the audio playback apparatus 1 and produces a service request including the acquired information and second personal profile information stored in the information processing apparatus 2. The control unit 210 of the information processing apparatus 2 transmits the produced service request to the health assist server 3-3 via the communication interface 241.

If the health assist server 3-3, which is one of service information providing apparatuses 3, receives the service request from the information processing apparatus 2, the health assist server 3-3 detects the number of steps for each user and for each day from the exercise information in the exercise execution history included in the service request. The health assist server 3-3 also calculates consumption energy (in calories) for each execution of exercise according to the formulae described above with reference to FIGS. 14 to 22.

The control unit 310 of the health assist server 3-3 produces graph information indicating the number of steps in the form of a bar graph and the consumption energy (in calories) in the form of a line graph as shown in FIG. 30A. Furthermore, the control unit 310 extracts proper advice information from a plurality of pieces of advice information registered in advance, in accordance with the exercise information indicating the number of steps and the consumption energy and the personal profile information indicating the age, the sex, the height, and the weight of the user. The control unit 310 produces display information including the graph information and the advice information such as that shown in FIG. 30A and transmits it to the information processing apparatus 2 which is the issuer of the request via the communication interface 331.

If the control unit 210 of the information processing apparatus 2 receives the service information (the display information) from the health assist server 3-3 via the communication interface 241, the control unit 210 supplies the received service information to the display 262 via the video output processing unit 261 to display the service information on the display screen 262G of the display 262 as shown in FIG. 30A.

This makes it possible for the user of the audio playback apparatus 1 to objectively determine whether the user is performing exercise every day in a proper manner or not. In other words, the user can perform exercise by an optimum amount according to the information displayed on the display 262, without having a risk of being ruined in health by too much exercise.

In the embodiment described above, advice information is selected from a plurality of pieces of advice information registered in advance. Alternatively, a skilled adviser such as a medical doctor, a nurse, a sport instructor, or a sport trainer having knowledge and/or a license may produce proper advice information in accordance with the amount of exercise performed by the user and the profile information, and may provide it to the user.

In a normal situation, advice may be selected from prepared advice in the above-described manner, but, when the user is anxious about something in exercise, the user may ask an adviser such as a medical doctor or a nurse to provide advice.

Not only the number of steps and the consumption energy (in calories), but the pulse rate and/or the respiration rate during exercise may also be sensed, and the sensed information may be stored as part of the exercise execution history in the audio playback apparatus 1. The exercise execution history is transmitted to the health assist server 3-3 via the information processing apparatus 2 to receive more detailed and more proper advice.

Event/Campaign Service

Figure 30B:
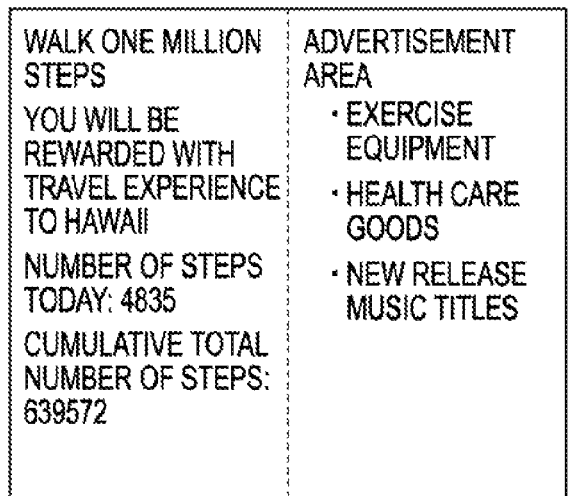

FIG. 30B illustrates event/campaign services provided by various servers which are service information providing apparatuses 3 located on the network 100. Servers located on the network 100, such as the music server 3-1, the exercise assist server 3-2, the health assist server 3-3, and the weblog server 3-4, may perform various kinds of events/campaigns for promotion or other purposes.

In a specific example described below, a particular server 3-X located on the network 100 performs a campaign in which an application for a lottery for a Hawaii travel is automatically made for a user of the audio playback apparatus 1 when the cumulative number of steps of walking, jogging, or running performed by the user while listening to music played by the audio playback apparatus 1 reaches one million.

Also in this example, as with music content service, each time the user of the audio playback apparatus 1 performs exercise such as walking, jogging, or running in synchronization with music played by the audio playback apparatus 1, an exercise execution history including information indicating music played and information indicating exercise performed is produced and stored in the storage device 53 of the audio playback apparatus 1.

If the user connects the audio playback apparatus 1 to the information processing apparatus 2 installed at the home of the user and performs a particular operation on the audio playback apparatus 1, the control unit 210 of the information processing apparatus 2 acquires the exercise execution history such as that shown in FIG. 13B and the first personal profile information from the audio playback apparatus 1 and produces a service request including the acquired information and second personal profile information stored in the information processing apparatus 2. The produced service request is transmitted via the communication interface 241 to the particular server 3-X which is one servers located on the network 100 and which is performing the campaign.

The server 3-X, which is one of servers located on the network 100 and which is performing the campaign, receives the service request from the information processing apparatus 2, and manages the cumulative number of steps described in the exercise information in the exercise execution history included in the service request, separately for each user. More specifically, the server 3-X manages the cumulative number of steps for each user by using, as key information, identification information uniquely identifying each user of the audio playback apparatus 1, such as a name of each user, included in the service request.

The control unit 310 of the server 3-X produces display information such that that shown in FIG. 30B. As shown in FIG. 30B, in an area on the left-hand side of the screen, event/campaign information is displayed, which includes an event/campaign title such as "WALK ONE MILLION STEPS AND GET REWARDED WITH TRAVEL EXPERIENCE TO HAWAII", text information "NUMBER OF STEPS WALKED TODAY", a numeric value indicating the number of steps walked today, and text information "CUMULATIVE TOTAL NUMBER OF STEPS", and a numeric value indicating the cumulative total number of steps. In an area on the right-hand side of the screen, advertisement information is displayed, which includes, for example, an advertisement of exercise equipment, an advertisement of health care goods, an advertisement of new release music titles, etc. The produced display information is transmitted to the information processing apparatus 2 which is the issuer of the request via the communication interface 331.

If the control unit 210 of the information processing apparatus 2 receives the service information (the display information) from the server 3-X via the communication interface 241, the control unit 210 supplies the received service information to the display 262 via the video output processing unit 261 to display the service information on the display screen 262G of the display 262 as shown in FIG. 30B.

Thus, from the information displayed as shown in FIG. 30B on the display screen 262G of the display 262 of the information processing apparatus 2, the user of the audio playback apparatus 1 can know the number of steps walked today, the cumulative total number of steps during a period from the point of time at which the history information was sent to the server 3-X for the first time to the current point of time, and the number of steps required to achieve the target number of steps. This motivates the user to continue the exercise.

When the cumulative total number of steps walked by the user reaches the target number of steps (one million steps in this specific example), the user of the audio playback apparatus 1 can automatically apply for participation in a travel to Hawaii provided as a reward in the event/campaign without having to send an application card or the like. When many users apply for participation in the travel to Hawaii, the server 3-X may determine winners of the prize by lot. The winners of the prize may be announced in many ways. For example, mail or e-mail may be sent to the winners, or information indicating the winners may be displayed on a Web page.

In the present embodiment, unlike conventional events/campaigns in which it is required to fill an application form and send it by mail, applicants do not need to do a troublesome application process. That is, in the present embodiment, when a user of the audio playback apparatus 1 performs exercise such as walking, jogging, or running while listening to music played by the audio playback apparatus 1, the history in terms of the number of steps is automatically recorded. By simply transmitting the history information to the server 3-X via the information processing apparatus 2, the cumulative number of steps is calculated by the server 3-X and an application for the event/campaign is automatically performed when the cumulative number of steps reaches a predetermined target value. Thus, the present embodiment provides a new method of applying for an event/campaign.

Service of Storing Weblog Information and Publishing Information

FIGS. 31A and 31B illustrate examples of services provided by the weblog server 3-4 which is one of service information providing apparatuses 3 shown in FIG. 1. In the service provided by the weblog server 3-4, unlike the services provided by the music server 3-1, the exercise assist server 3-2, or the health assist server 3-3, it is necessarily needed to prepare in advance information to be provided to the information processing apparatus 2. Instead, the weblog server 3-4 provides a service in which profile information and/or history information included in service requests received via information processing apparatuses 2 are stored and put on view to a large number of unspecified persons who access the information from their information processing apparatus via the network 100.

Also in this example, as with music content service, each time the user of the audio playback apparatus 1 performs exercise such as walking, jogging, or running in synchronization with music played by the audio playback apparatus 1, an exercise execution history including information indicating music played and information indicating exercise performed is produced and stored in the storage device 53 of the audio playback apparatus 1.

If the user connects the audio playback apparatus 1 to the information processing apparatus 2 installed at the home of the user and performs a particular operation on the audio playback apparatus 1, the control unit 210 of the information processing apparatus 2 acquires the exercise execution history such as that shown in FIG. 13B and the first personal profile information from the audio playback apparatus 1 and produces a service request including the acquired information and second personal profile information stored in the information processing apparatus 2. The control unit 210 of the information processing apparatus 2 transmits the produced service request to the weblog server 3-4 via the communication interface 241. In the present embodiment, the user of the audio playback apparatus 1 may 3produce a comment including about, for example, 200characters on the information processing apparatus 2 and may incorporate the comment into the service request.

If the control unit 310 of the weblog server 3-4 receives the service request from the information processing apparatus 2 via the communication interface 331, the control unit 310 extracts, from the received service request, necessary information such as first personal profile information, second personal profile information, an exercise execution history, an exercise plan history, comment information, an exercise execution date, etc.

On the basis of the extracted information, the control unit 310 of the weblog server 3-4 produces history information for use as information accessible on a weblog site, separately for each user of the audio playback apparatus 1 and stores it in the history information storage unit 351. The history information produced may include, for example, the exercise execution date, the comment, tittles (A, B, C, and so on) of played music described in the exercise execution history, the number of steps walked today, and the energy consumed today, as in the example shown in FIG. 31A. Note that, of various items of the history information to be published on the publicly accessible weblog site, the consumption energy in calories can be calculated in the above-described manner, and other items can be extracted from the service request.

The weblog history information stored in the history information storage unit 351 of the weblog server 3-4 is then given a title such as "Exercise Diary" as in the example shown in FIG. 31B and published on the weblog site accessible to the public.

As described above, the weblog server 3-4 provide two services in one of which history information to be published on the publicly accessible weblog site is produced by extracting from information provided from the audio playback apparatus 1 via the information processing apparatus 2 and/or by processing extracted information as necessary, and the produced history information is stored, and in the other one of which history information stored in the weblog server 3-4 is published on the weblog site such that any person is allowed to access the history information.

In the health exercise assist system according to the present embodiment, as described above with reference to FIGS. 29 to 31, when the user of the audio playback apparatus 1 performs exercise while listening to music played by the audio playback apparatus 1 worn on the user of the audio playback apparatus 1, exercise execution history is automatically produced and stored, and a service request including this history information is produced and transmitted to the particular server on the network 100 via the information processing apparatus 2 thereby allowing the user of the audio playback apparatus 1 to receive service provided by the server, depending on the information included in the history information.

In the health exercise assist system according to the present embodiment, the user is allowed to receive various kinds of services depending on the amount of exercise performed, and the user is allowed to easily publish history information in terms of exercise performed by the user on the publicly accessible weblog site. Thus, the service provided by the health exercise assist system gives an incentive to the user to continue the exercise to enhance health.

The health exercise assist system may timely provide the user with information on music or exercise equipment suitable for use in exercise. The health exercise assist system may manage exercise history information in a manner that allows the user to easily use the exercise history information thereby making it possible to manage health of the user.

The health exercise assist system may hold an event/campaign in which the user of the audio playback apparatus 1 is allowed to participate to enhance health. That is, it is possible to configure the health exercise assist system in many ways depending on the purpose.

The health exercise assist system may extract advertisements likely to be useful for a user who performs exercise from a huge number of advertisements and may provide the extracted advertisements to the user.

Modifications of Health Exercise Assist System

Now, modifications to the health exercise assist system are described below with reference to FIGS. 32 and 33. The health exercise assist system according to the embodiment described above includes, as shown in FIG. 1, the audio playback apparatus 1, the information processing apparatus 2, and one or more service information providing apparatuses 3 located on the network 100. In this embodiment, as described above, the information processing apparatus 2 is a personal computer or the like having a communication capability and is installed at the home or the like of the user of the audio playback apparatus 1. However, the health exercise assist system does not necessary need to include the information processing apparatus 2.

Figure 32:
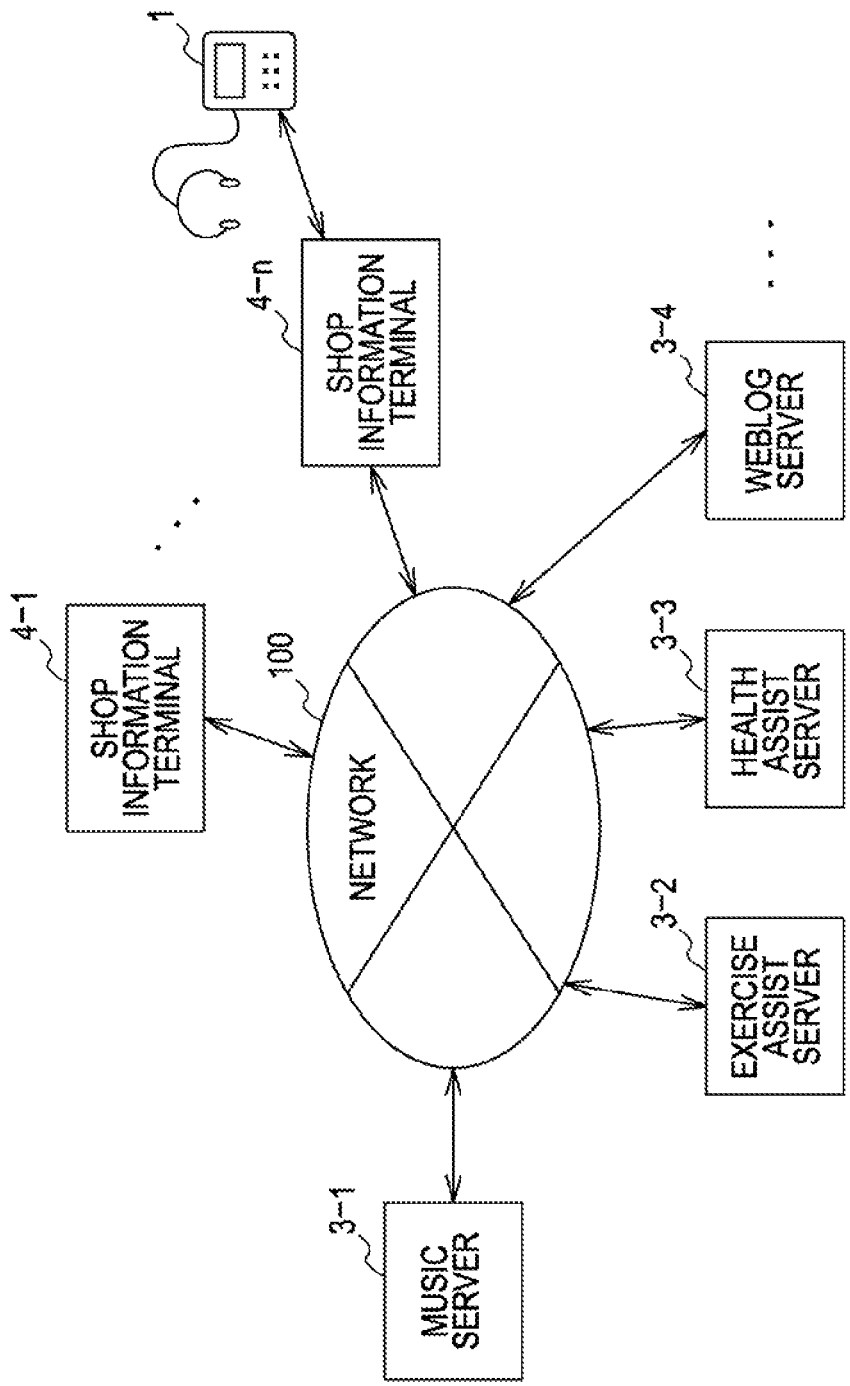
FIG. 32 is diagram illustrating a modification of a health exercise assist system.

For example, as shown in FIG. 32, a health exercise assist system may be configured so as to include an audio playback apparatus 1, shop information terminals 4-1, 4-2, . . . , 4-*n*, and service information providing apparatuses 3 such as an audio server 3-1, an exercise assist server 3-2, a health assist server 3-3, and a weblog server 3-4.

The shop information terminals 4-1 to 4-*n* shown in FIG. 32 are installed in various types of shops such as convenience stores, CD (Compact Disc) shops, video rental shops, etc. Each shop information terminal is basically similar in function to the information processing apparatus 2 according to the embodiment described above, although there is some difference necessary to make it possible for these shop information terminals 4-1 to 4-*n* to be used by a large number of unspecified persons. Hereinafter, when it is not necessary to distinguish among shop information terminals 4-1 to 4-*n*, they will be denoted as shop information terminals 4.

Each of the shop information terminals 4-1 to 4-*n* shown in FIG. 32 has various capabilities including a capability of connecting to a network, a capability of connecting to the audio playback apparatus 1, a capability of reading profile information, history information, and other information from the audio playback apparatus 1, a capability of producing a service request including the acquired profile information and/of the history information, a capability of transmitting the produced service request to a particular server, capability of receiving service information or the like returned from the server, and a capability of transferring the received service information or the like to the connected audio playback apparatus 1.

Note that although each of the shop information terminals 4-1 to 4-*n* has the capability of transferring the received service information or the like to the connected audio playback apparatus 1, the information processing apparatus 2 described above with reference to FIG. 1 does not have this capability. This capability makes it possible to use each of the shop information terminals 4-1 to 4-*n* in a highly efficient manner without being occupied by some of many unspecified persons for a long time. The information transferred to the audio playback apparatus 1 may be displayed on the display screen 34G of the display 34 of the audio playback apparatus 1 so that the user of the audio playback apparatus 1 can see it on the display screen 34G, or the information may be further transferred from the audio playback apparatus 1 to an information processing apparatus 2 such as a personal computer installed at the home of the user so that the information is displayed or printed out to allow the user to read the information.

Instead of transferring the service information received from the service information providing apparatus 3 to the audio playback apparatus 1, the shop information terminal 4 may print out the received service information or the like on paper or may display the service information on the display screen of the display of the shop information terminal 4 as with the information processing apparatus 2. Thus, each shop information terminal 4 has substantially similar capabilities to those of the information processing apparatus 2 shown in FIG. 25.

In the health exercise assist system configured as shown in FIG. 32, for example, when the user of the audio playback apparatus 1 performs exercise at a place the user visits while listening to music played by the audio playback apparatus 1 worn on the user, the user may bring the audio playback apparatus 1, after the exercise is completed, to a nearby shop wherein a shop information terminal 4 is installed, to receive desired service information. That is, after the audio playback apparatus 1 is used at a remote place, the user of the audio playback apparatus 1 does not have to bring the audio playback apparatus 1 to the home to transmit/receive information to/from the service information providing apparatus 3 via the information processing apparatus 2 installed at the home of the user, but it is possible to receive a service from the service information providing apparatus 3 by using a nearby shop information terminal 4.

Figure 33:
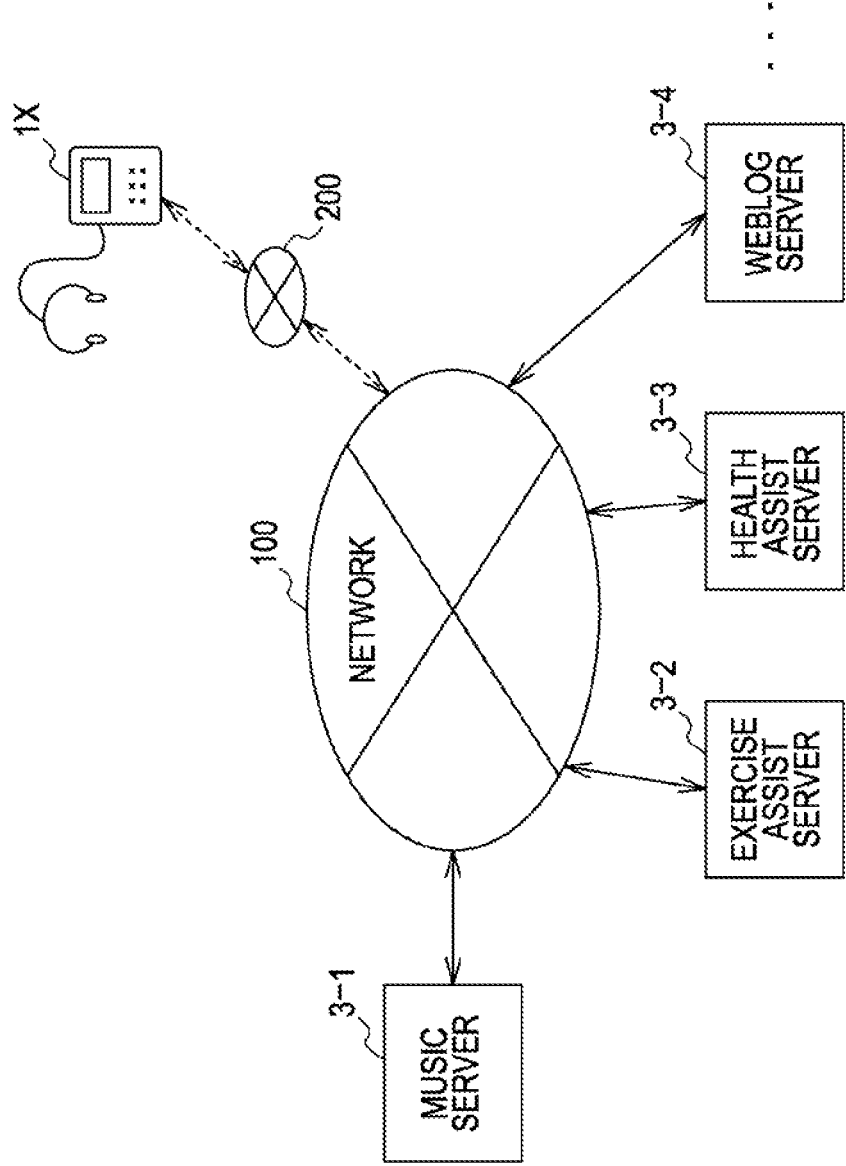
FIG. 33 is diagram illustrating a modification of the health exercise assist system.

In an example shown in FIG. 33, a health exercise assist system includes an audio playback apparatus 1X and a plurality of service information providing apparatuses 3 such as an audio server 3-1, an exercise assist server 3-2, a health assist server 3-3, and a weblog server 3-4, but the health exercise assist system includes neither an information processing apparatus 2 nor a shop information terminal 4.

In this health exercise assist system shown in FIG. 33, the audio playback apparatus 1-X has a communication capability that allows the audio playback apparatus 1-X to directly transmit a service request including an exercise execution history and personal profile information produced by the audio playback apparatus 1-X to a particular service information providing apparatus 3. The communication capability also allows the audio playback apparatus 1-X to directly receive service information or the like returned from the service information providing apparatus 3. The received service information may be displayed on a display of the audio playback apparatus 1-X so that the user can read it.

Figure 34:
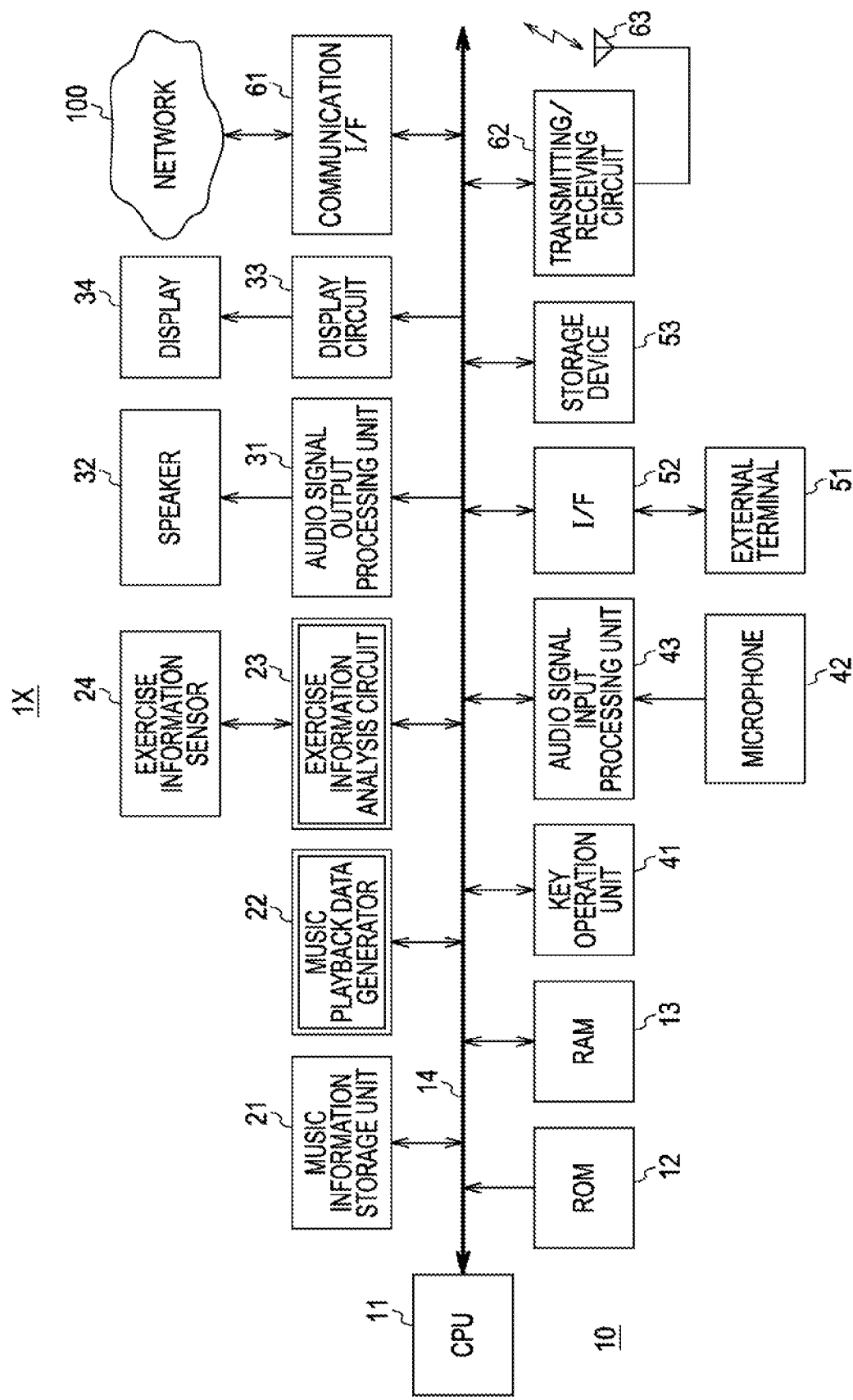
FIG. 34 is a block diagram illustrating an example of a configuration of an audio playback apparatus in a health exercise assist system.

FIG. 34 is a block diagram illustrating an example of a configuration of the audio playback apparatus 1-X in the health exercise assist system shown in FIG. 33. As can be seen from comparison between FIG. 34 and FIG. 2, the audio playback apparatus 1-X shown in FIG. 34 is similar in configuration to the audio playback apparatus 1 shown in FIG. 2 except that the audio playback apparatus 1-X additionally includes a communication interface 61, a transmitting/receiving circuit 62 and a transmitting/receiving antenna 63. In the audio playback apparatus 1-X shown in FIG. 34, similar parts to those in the audio playback apparatus 1 shown in FIG. 2 are denoted by similar reference numerals, and a duplicated explanation thereof is omitted herein.

In the audio playback apparatus 1-X shown in FIG. 34, the communication interface 61 makes it possible for the audio playback apparatus 1-X to connect to a wide-area network to transmit/receive various kinds of data. As with the audio playback apparatus 1 shown in FIG. 2, the audio playback apparatus 1-X is of a portable type and is designed to be used in a state in which the audio playback apparatus 1-X is put in a pocket of clothes of a user or is worn on the user who is performing exercise such as walking, jogging, or running.

Thus, as shown in FIG. 33, the audio playback apparatus 1-X is capable of connecting via the communication interface 61 to a network 100 such as the Internet via a portable communication terminal network such as a portable telephone network 200 thereby making it possible to access various service information providing apparatuses 3 located on the network 100.

In the present embodiment, the audio playback apparatus 1-X is capable of connecting, via the transmitting/receiving circuit 62 and the transmitting/receiving antenna 63, to a wireless LAN (Local Area Network) and further therefrom to the Internet or another apparatus connected to the wireless LAN to transmit/receive data to/from the apparatus.

In the health exercise assist system shown in FIG. 33, if the user of the audio playback apparatus 1-X exercises while listening to music played by the audio playback apparatus 1-X worn on the user, then, as with the audio playback apparatus 1 described above with reference to FIG. 2, information such as an exercise plan history and an exercise execution history is stored in the storage device 53.

Furthermore, in the present embodiment, has both first personal profile information and second personal profile information are stored in the audio playback apparatus 1-X. If the user inputs via the key operation unit 41 a command to produce and transmit a service request, then, in accordance with the command, the control unit 10 produces a service request including the personal profile information, the exercise plan history, and the exercise execution history and transmits the produced service request to a particular one of the service information providing apparatuses 3 located on the network 100 via the communication interface 61.

Note that the service request also includes information necessary to perform communication between the information processing apparatus 2 and the service information providing apparatus 3, such as address information identifying the service information providing apparatus 3 which is a destination of the service request and address information identifying the information processing apparatus 2 which is a sender of the service request. The address information necessary in the above-described transmission process is acquired from the storage device 53 of the audio playback apparatus 1-X.

If service information or the like transmitted from the service information providing apparatus 3 in response to the service request is received via the communication interface 61, the control unit 10 of the audio playback apparatus 1-X displays the received service information on the display screen 34G of the display 34 via the display circuit 33 so that the user can read it.

As described above, the health exercise assist system configured as shown in FIG. 33 allows users to receive various kinds of services provided by service information providing apparatuses at any time and at any place.

Other Methods of Calculating Amount of Exercise

In the embodiments described above, consumption energy in calories is calculated based on the input personal profile information, the tempo of music played when exercise is performed, and the exercise time as described above with reference to FIGS. 14 to 16, or based on the weight of the user described in the input personal profile information, the MET value, and the exercise time as described above with reference to FIG. 17. However, the methods of calculating consumption energy are not limited to those. For example, consumption energy may be calculated in a simpler manner, as described below.

FIG. 35 illustrates an example of a simplified method of calculating consumption energy.

In a first specific example, consumption energy is calculated for a case in which a user walks as exercise. In this calculation, the step size in the walking is assumed to be equal to an average value 0.7 m (70 cm). In this case, the consumption energy in calories can be given by 0.5×weight×walking distance (moving distance) according to formula (33) in FIG. 35. The consumption energy in calories may also be calculated using the number of steps instead of the walking distance. In this case, the consumption energy in calories can be given by 0.00035×weight×number of steps according to formula (34) in FIG. 35.

In a second example of calculation of energy consumed during walking, the walking speed is assumed to be equal to an average value 4 km/hour. In this case, the consumption energy in calories can be given by 0.5×weight×walking distance (moving distance) according to formula (35) in FIG. 35. The consumption energy in calories may also be calculated using the exercise time instead of the walking distance. In this case, the consumption energy in calories can be given by 0.033×weight×exercise time according to formula (36) in FIG. 35.

In a third example, energy consumed during jogging is calculated. In this calculation, the walking step size is assumed to be equal to an average value 0.7 m (70 cm). In this case, the consumption energy in calories can be given by 1.0×weight×walking distance (moving distance) according to formula (37) in FIG. 35. The consumption energy in calories can also be calculated using the number of steps instead of the walking distance. In this case, the consumption energy in calories can be given by 0.0007×weight×number of steps according to formula (38) in FIG. 35.

In a fourth example of calculation of energy consumed during jogging, the moving speed is assumed to be equal to an average value 8 km/hour. In this case, the consumption energy in calories can be given by 1.0×weight×walking distance (moving distance) according to formula (39) in FIG. 35. The consumption energy in calories may also be calculated using the exercise time instead of the walking distance. In this case, the consumption energy in calories can be given by 0.13×weight×exercise time according to formula (40) in FIG. 35.

As described above, by using the walking speed or the number of steps assumed to be equal to an average value, it becomes possible to calculate energy consumed during exercise in a simplified manner as shown in FIG. 35.

Use of the simplified formula makes it possible to determine the amount of exercise without imposing a significant processing load on the CPU. This allows a reduction in size and consumption power of a device for calculating the amount of exercise expressed in consumed calories.

Other Embodiments

In the embodiments described above, it is assumed that the user performs walking, jogging, or running as exercise. However, the exercise is not limited to these three types. The present invention may be applied to a wide variety of exercise types such as a walking exercise group such as walking, jogging, running, dash, etc., a group of exercise types which can be performed for a rather long time, such as cycling, boating, jumping rope, etc., muscle training such as abdominal muscle training, back muscle training, press-up exercise, etc.

As for information associated with the amount of exercise, one or more of items needed by the user are selected from the exercise time, the walking distance or the moving distance, the average speed, the consumption energy (in calories), the amount of fat burnt, etc., and the calculated values are displayed. In addition, the pulse rate, the blood pressure, the temperature, etc. may be detected using sensors and the detected values may be displayed.

The personal profile information may include at least the name, the age, the height, and the weight of a user. The walking step size may be accurately measured, and the result may be included in the personal profile information. The personal profile information may further include the pulse rate, the blood pressure, and the temperate in the resting state. These values may be input by a user or may be automatically sensed.

The music information list is not limited to that shown in FIG. 9. The music information list may include additional information such as a release date of each piece of music, a popularity rank, etc. Such additional information may be provided to an audio playback apparatus of a user from a music database of a server on the network 100, or may be provided via a storage medium such as a CD (Compact Disc), DVD (Digital Versatile Disc), or a semiconductor memory.

As described above, various types of storage media such as an optical disk such as a CD or DVD, a magneto-optical disk such as a MD (Mini Disc (trademark)) disk, a magnetic tape, a hard disk, a semiconductor memory, or an IC memory card can be used as the storage medium of the music information storage unit 21 or the storage device 53 in the audio playback apparatus 1 or 1-X.

In the audio playback apparatus 1 or 1-X according to the embodiments described above, information such as the music information list, the history information, etc. is stored in the storage medium of the music information storage unit 21 or the storage device 53. Alternatively, some or all information may be stored in a nonvolatile memory such as EEPROM (Electrically Erasable and Programmable ROM) or a flash memory disposed in the control unit 10.

In the embodiments described above, the audio playback apparatus 1 produces a service request including an exercise plan history, an exercise execution history, and personal profile information and transmits the produced service request to the service information providing apparatus 3. Alternatively, the service request may include only necessary information. For example, the service request transmitted to the service information providing apparatus may include at least one of the exercise plan history, the exercise execution history, and the music playback history.

That is, the service request transmitted from the information processing apparatus 2 or the audio playback apparatus 1-X to the service information providing apparatus 3 may include only information needed by the service information providing apparatus 3. For example, when only the cumulative number of steps walked is needed, the exercise execution history transmitted to the service information providing apparatus 3 may include only the number of steps walked. In a case where consumption energy in calories is needed, the audio playback apparatus 1 or 1-X or the information processing apparatus 2 may calculate the consumption energy in calories and may include the calculated consumption energy in calories in the service request transmitted to the service information providing apparatus 3. Alternatively, the service information providing apparatus 3 may calculate the consumption energy in calories based on information included in the service request.

In a case where the service information providing apparatus 3 is capable of managing the history information separately for each user of the audio playback apparatus 1, fixed items such as the name, the age, etc. in the personal profile information may be stored in advance in the service information providing apparatus 3 and may be managed by the service information providing apparatus 3. In this case, the service request does not need to include these items.

The service request needs to include address information identifying the service information providing apparatus 3 specified as the destination and address information identifying the information processing apparatus 2 or the audio playback apparatus 1-X. This ensures that the service request is correctly transmitted to the service information providing apparatus identified by the address information, and the information is returned in response to the service request to the correct destination identified by the address information included in the service request.

In the embodiments described above, it is assumed that music data is played back, but data played back is not limited to music data. The present invention may also be applied to an apparatus in which AV (audio/visual) data is played back such that video data included in the AV data is displayed on a display (such as the display 34) via a display circuit (such as the display circuit 33) in synchronization with music data included in the AV data.

The audio playback apparatus 1 or 1-X may further have a capability of automatically producing a list of music to be played during exercise, from a target exercise time or a target amount of exercise input in advance by a user, and this capability may be used in conjunction with other capabilities described above. Candidates for music to be played may be determined from exercise information input by a user and may be presented to the user. In this case, the exercise information may be determined from information output from the exercise sensor in a similar manner to the case where the exercise tempo is determined from the information output from the exercise sensor.

Music data which matches the tempo of the motion of a user is automatically selected and played. A user may prepare in advance a list of music to be played depending on an exercise type, an exercise time, and exercise strength. In this case, the exercise information may be determined in a similar manner to the example described above. The audio playback apparatus 1 or 1-X may also be used in circuit training or the like.

It should be understood by those skilled in the art that various modifications, combinations, sub-combinations and alterations may occur depending on design requirements and other factors insofar as they are within the scope of the appended claims or the equivalents thereof.

What is claimed is:

1. A health exercise assist system including a portable music playback apparatus, a service information providing apparatus, and an information processing apparatus, the system comprising:
the portable music playback apparatus including
a detection unit adapted to detect exercise information associated with physical exercise performed by a user,
a music playback unit adapted to select music to be played and play the selected music,
a storage unit adapted to store a preset exercise plan, a history of exercise information detected by the detection unit, and a music playback history of music played by the music playback unit, and
an information output unit adapted to output information stored in the storage unit;
the service information providing apparatus including
an information input unit adapted to receive information from the portable music playback apparatus via the information processing apparatus, the information including the history of exercise information and the music playback history which is associated with the history of exercise information to indicate the selected music played during the physical exercise performed by the user,
a service information producing unit adapted to estimate a total amount of exercise performed by the user during playback of the selected music using a play time and tempo of the selected music and a height of the user specified in a user profile, the service information producing unit further adapted to produce service information to be provided to the user of the portable music playback apparatus, the service information including a service or data reward based upon the estimated total amount of exercise performed, and
a service information output unit adapted to output the service information; and
the information processing apparatus including
an information input unit adapted to receive information from the portable music playback apparatus, the information including the history of exercise information and the music playback history,
a transmitting unit adapted to transmit the information received by the information input unit to the service information providing apparatus,
a receiving unit adapted to receive the service information output from the service information providing apparatus, and
means for providing the service information to the user.

2. The health exercise assist system according to claim 1, wherein the service information produced by the service information producing unit further includes at least information associated with a music content playable by the portable music playback apparatus.

3. The health exercise assist system according to claim 1, wherein the service information produced by the service information producing unit further includes at least information suggesting a next target amount of exercise.

4. The health exercise assist system according to claim 1, wherein the service information produced by the service information producing unit further includes health management information based on an amount of exercise.

5. The health exercise assist system according to claim 1, wherein the service information produced by the service information producing unit is associated with an application for an event/campaign based on an amount of exercise according to one or both of the history of the exercise information and the music playback history.

6. A portable music playback apparatus in a health exercise assist system including the portable music playback apparatus, a service information providing apparatus, and an information processing apparatus, comprising:
a detection unit adapted to detect exercise information associated with physical exercise performed by a user;
a music playback unit adapted to select music to be played and play the selected music;
a storage unit adapted to store a preset exercise plan, a history of exercise information detected by the detection unit, and a music playback history of music played by the music playback unit;
an information output unit adapted to output the history of exercise information and the music playback history to the information processing apparatus, the music playback history associated with the history of exercise information to indicate the selected music played during the physical exercise performed by the user; and
a receiving unit adapted to receive service information output from the service information providing apparatus, the service information including a service or data reward based upon an estimated total amount of exercise performed by the user during playback of the selected music which is determined using a play time and tempo of the selected music, and a height of the user specified in a user profile.

7. A service information providing apparatus in a health exercise assist system including a portable music playback apparatus, the service information providing apparatus, and an information processing apparatus, comprising:
an information input unit adapted to receive information from the portable music playback apparatus via the information processing apparatus, the information including a history of exercise information and a music playback history which is associated with the history of exercise information to indicate the selected music played during a physical exercise performed by a user;
a service information producing unit adapted to estimate a total amount of exercise performed by the user during playback of the selected music using a play time and tempo of the selected music and a height of the user specified in a user profile, the service information producing unit further adapted to produce service information to be provided to the user of the portable music playback apparatus, the service information including a service or data reward based upon the estimated total amount of exercise performed; and a service information output unit adapted to output the service information.

8. An information processing apparatus in a health exercise assist system including a portable music playback apparatus, a service information providing apparatus, and the information processing apparatus, comprising:

an information input unit adapted to receive information from the portable music playback apparatus, the information including a history of exercise information and a music playback history which is associated with the history of exercise information to indicate the selected music played during a physical exercise performed by a user;

a transmitting unit adapted to transmit the information received by the information input unit to the service information providing apparatus;

a receiving unit adapted to receive service information output from the service information providing apparatus, the service information including a service or data reward based upon an estimated total amount of exercise performed by the user during playback of the selected music, the estimated total amount of exercise performed using a play time and tempo of the selected music and a height of the user specified in a user profile; and means for providing the service information to a user.

9. A health exercise assist system including a portable music playback apparatus and a service information providing apparatus, the system comprising:

the portable music playback apparatus including a detection unit adapted to detect exercise information associated with physical exercise performed by a user, a music playback unit adapted to select music to be played and play the selected music, a storage unit adapted to store a preset exercise plan, a history of exercise information detected by the detection unit, and a music playback history of music played by the music playback unit, a transmitting unit adapted to transmit information to the service information providing apparatus, the information including the history of exercise information and the music playback history, a receiving unit adapted to receive service information output from the service information providing apparatus, and means for providing the service information to the user; and the service information providing apparatus including an information input unit adapted to receive information from the transmitting unit of the portable music playback apparatus, the information including the history of exercise information and the music playback history which is associated with the history of exercise information to indicate the selected music played during the physical exercise performed by the user, a service information producing unit adapted to estimate a total amount of exercise performed by the user during playback of the selected music using a play time and tempo of the selected music and a height of the user specified in a user profile, the service information producing unit further adapted to produce service information to be provided to the user of the portable music playback apparatus, the service information including a service or data reward based upon the estimated total amount of exercise performed, and a service information output unit adapted to output the service information to the portable music playback apparatus.

10. A portable music playback apparatus in a health exercise assist system including the portable music playback apparatus and a service information providing apparatus, comprising:

a detection unit adapted to detect exercise information associated with physical exercise performed by a user;

a music playback unit adapted to select music to be played and play the selected music;

a storage unit adapted to store a preset exercise plan, a history of exercise information detected by the detection unit, and a music playback history of music played by the music playback unit;

a transmitting unit adapted to transmit information to the service information providing apparatus, the information including the history of exercise information and the music playback history which is associated with the history of exercise information to indicate the selected music played during the physical exercise performed by the user;

a receiving unit adapted to receive service information output from the service information providing apparatus, the service information including a service or data reward based upon an estimated total amount of exercise performed by the user during playback of the selected music, the estimated total amount of exercise determined using a play time and tempo of the selected music and a height of the user specified in a user profile; and means for providing the service information to the user.

11. A service information providing apparatus in a health exercise assist system including a portable music playback apparatus and the service information providing apparatus, comprising:

an information input unit adapted to receive information from the transmitting unit of the portable music playback apparatus, the information including the history of exercise information and the music playback history which is associated with the history of exercise information to indicate the selected music played during a physical exercise performed by a user;

a service information producing unit adapted to estimate a total amount of exercise performed by the user during playback of the selected music using a play time and tempo of the selected music and a height of the user specified in a user profile, the service information producing unit further adapted to produce service information to be provided to the user of the portable music playback apparatus, the service information including a service or data reward based upon the estimated total amount of exercise performed; and a service information output unit adapted to output the service information to the portable music playback apparatus.

12. A portable music playback apparatus, comprising:

a music information storage unit adapted to store playable music data and attribute information associated with the music data;

means for accepting an input of an exercise plan;

an exercise plan storage unit adapted to store the exercise plan;

a playlist producing unit adapted to produce a playlist by selecting music data suitable for the exercise plan in accordance with the attribute information associated with the music data;

a detection unit adapted to detect exercise information associated with physical exercise performed by a user;

a music playback unit adapted to select music data to be played in accordance with the exercise plan, the playlist, and the exercise information, and to play the selected music data;

a music playback history storage unit adapted to store a music playback history of the music played by the music playback unit;

an exercise history storage unit adapted to store a history of the exercise information;

an information output unit adapted to output the history of exercise information and the music playback history which is associated with the history of exercise information to indicate the selected music played during a physical exercise performed by a user; and a receiving unit adapted to receive service information output from the service information providing apparatus, the service information including a service or data reward based upon an estimated total amount of exercise performed, the estimated total amount of exercise determined using a play time and tempo of the selected music and a height of the user specified in a user profile.

13. A health exercise assist method in a health exercise assist system including a portable music playback apparatus, a service information providing apparatus, and an information processing apparatus, the method comprising:

in the portable music playback apparatus, selecting music to be played and playing the selected music, detecting exercise information associated with physical exercise performed by a user in synchronization with the playing the selected music, storing, in a storage unit, a preset exercise plan, a history of exercise information detected in the detecting, and a music playback history of music played in the playing the selected music, and outputting information stored in the storage unit to the information processing apparatus; and in the service information providing apparatus, receiving information from the portable music playback apparatus via the information processing apparatus, the information including the history of exercise information and the music playback history which is associated with the history of exercise information to indicate the selected music played during a physical exercise performed by a user, estimating a total amount of exercise performed by the user during playback of the selected music using a play time and tempo of the selected music and a height of the user specified in a user profile, producing service information to be provided to the user of the portable music playback apparatus, the service information including a service or data reward based upon the estimated total amount of exercise performed, and outputting the service information to the information processing apparatus; and, in the information processing apparatus, transmitting the information received in the receiving information from the portable music playback apparatus to the service information providing apparatus, receiving the service information output from the service information providing apparatus, and providing the service information to the user.

14. A health exercise assist method in a health exercise assist system including a portable music playback apparatus and a service information providing apparatus, the method comprising:

in the portable music playback apparatus, selecting music to be played and playing the selected music, detecting exercise information associated with physical exercise performed by a user in synchronization with the playing the selected music, storing, in a storage unit, a preset exercise plan, a history of exercise information detected in the detecting, and a music playback history of music played in the playing the selected music, transmitting information to the service information providing apparatus, the information including the history of exercise information and the music playback history, receiving service information output from the service information providing apparatus, and providing the service information to the user; and in the service information providing apparatus, receiving information from the portable music playback apparatus, the information including the history of exercise information and the music playback history which is associated with the history of exercise information to indicate the selected music played during a physical exercise performed by a user, estimating a total amount of exercise performed by the user during playback of the selected music using a play time and tempo of the selected music and a height of the user specified in a user profile, producing service information to be provided to the user of the portable music playback apparatus, the service information including a service or data reward based upon the estimated total amount of exercise performed, and outputting the service information to the portable music playback apparatus.

15. A health exercise assist system including a portable music playback apparatus, a service information providing apparatus, and an information processing apparatus, the system comprising:

the portable music playback apparatus including a detection unit adapted to detect exercise information associated with physical exercise performed by a user, a music playback unit adapted to select music to be played and play the selected music, a storage unit adapted to store a preset exercise plan, a history of exercise information detected by the detection unit, and a music playback history of music played by the music playback unit, and an information output unit adapted to output information stored in the storage unit, the service information providing apparatus including an information input unit adapted to receive information from the portable music playback apparatus via the information processing apparatus, the information including the history of exercise information and the music playback history which is associated with the history of exercise information to indicate the selected music played during a physical exercise performed by a user, a service information producing unit adapted to estimate a total amount of exercise performed by the user during playback of the selected music using a play time and tempo of the selected music and a height of the user specified in a user profile, the service information producing unit further adapted to produce service information to be provided to the user of the portable music playback apparatus, the service information including a service or data reward based upon the estimated total amount of exercise performed, and a service information output unit adapted to output the service information; and the information processing apparatus including an information input unit adapted to receive information from the portable music playback apparatus, the information including the history of exercise information and the music playback history, a transmitting unit adapted to transmit the information received by the information input unit to the service information providing apparatus, a receiving unit adapted to receive the service information output from the service information providing apparatus, and a providing unit adapted to provide the service information to the user.

16. An information processing apparatus in a health exercise assist system including a portable music playback apparatus, a service information providing apparatus, and the information processing apparatus, comprising:

an information input unit adapted to receive information from the portable music playback apparatus, the information including a history of exercise information and a music playback history which is associated with the history of exercise information to indicate the selected music played during a physical exercise performed by a user;

a transmitting unit adapted to transmit the information received by the information input unit to the service information providing apparatus;

a receiving unit adapted to receive service information output from the service information providing apparatus, the service information including a service or data reward based upon estimated total amount of exercise performed, the estimated total amount of exercise determined using a play time and tempo of the selected music and a height of the user specified in a user profile; and a providing unit adapted to provide the service information to a user.

17. A health exercise assist system including a portable music playback apparatus and a service information providing apparatus, the system comprising:

the portable music playback apparatus including a detection unit adapted to detect exercise information associated with physical exercise performed by a user, a music playback unit adapted to select music to be played and play the selected music, a storage unit adapted to store a preset exercise plan, a history of exercise information detected by the detection unit, and a music playback history of music played by the music playback unit, a transmitting unit adapted to transmit information to the service information providing apparatus, the information including the history of exercise information and the music playback history, a receiving unit adapted to receive service information output from the service information providing apparatus, and a providing unit adapted to provide the service information to the user; and the service information providing apparatus including an information input unit adapted to receive information from the transmitting unit of the portable music playback apparatus, the information including the history of exercise information and the music playback history which is associated with the history of exercise information to indicate the selected music played during a physical exercise performed by a user, a service information producing unit adapted to estimate a total amount of exercise performed by the user during playback of the selected music using a play time and tempo of the selected music and a height of the user specified in a user profile, the service information producing unit further adapted to produce service information to be provided to the user of the portable music playback apparatus, the service information including a service or data reward based upon the estimated total amount of exercise performed, and a service information output unit adapted to output the service information to the portable music playback apparatus.

18. A portable music playback apparatus in a health exercise assist system including the portable music playback apparatus and a service information providing apparatus, comprising:

a detection unit adapted to detect exercise information associated with physical exercise performed by a user;

a music playback unit adapted to select music to be played and play the selected music;

a storage unit adapted to store a preset exercise plan, a history of exercise information detected by the detection unit, and a music playback history of music played by the music playback unit;

a transmitting unit adapted to transmit information to the service information providing apparatus, the information including the history of exercise information and the music playback history which is associated with the history of exercise information to indicate the selected music played during a physical exercise performed by a user;

a receiving unit adapted to receive service information output from the service information providing apparatus, the service information including a service or data reward based upon an estimated total amount of exercise performed, the estimated total amount of exercise determined using a play time and tempo of the selected music and a height of the user specified in a user profile; and a providing unit adapted to provide the service information to the user.

19. A portable music playback apparatus, comprising:

a music information storage unit adapted to store playable music data and attribute information associated with the music data;

an input accepting unit adapted to accept an input of an exercise plan;

an exercise plan storage unit adapted to store the exercise plan;

a playlist producing unit adapted to produce a playlist by selecting music data suitable for the exercise plan in accordance with the attribute information associated with the music data;

a detection unit adapted to detect exercise information associated with physical exercise performed by a user;

a music playback unit adapted to select music data to be played in accordance with the exercise plan, the playlist, and the exercise information, and to play the selected music data;

a music playback history storage unit adapted to store a music playback history of the music played by the music playback unit;

an exercise history storage unit adapted to store a history of the exercise information;

an information output unit adapted to output the history of exercise information and the music playback history which is associated with the history of exercise information to indicate the selected music played during a physical exercise performed by a user; and a receiving unit adapted to receive service information output from a service information providing apparatus, the service information including a service or data reward based upon an estimated total amount of exercise performed by the user during playback of the selected music, the estimated total amount of exercise determined using a play time and tempo of the selected music and a height of the user specified in a user profile.

* * * * *